United States Patent [19]
Magal

[11] Patent Number: 5,929,041
[45] Date of Patent: *Jul. 27, 1999

[54] METHOD FOR PREVENTING AND TREATING SENSORINEURAL HEARING LOSS AND VESTIBULAR DISORDERS USING GLIAL CELL LINE-DERIVED NEUROTROPHIC FACTOR(GDNF) PROTEIN PRODUCT

[75] Inventor: Ella Magal, Thousand Oaks, Calif.

[73] Assignee: Amgen Inc., Thousand Okas, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/710,219

[22] Filed: Sep. 13, 1996

Related U.S. Application Data

[63] Continuation-in-part of application No. 08/606,176, Feb. 23, 1996, Pat. No. 5,837,681.

[51] Int. Cl.$^6$ .......................... A01N 63/00; A01N 37/18; A61K 38/00; A61K 48/00
[52] U.S. Cl. ............................ 514/44; 514/2; 424/93.2; 424/93.21; 935/62
[58] Field of Search ......................... 514/44, 2; 536/23.1, 536/23.5; 435/320.1, 375; 424/93.21, 93.2; 935/62

[56] References Cited

U.S. PATENT DOCUMENTS

| | | | |
|---|---|---|---|
| 4,518,584 | 5/1985 | Mark et al. | 424/85.2 |
| 5,106,627 | 4/1992 | Aebischer et al. | 424/424 |
| 5,653,975 | 8/1997 | Baetge et al. | 424/93.1 |
| 5,658,785 | 8/1997 | Johnson | 435/367 |

FOREIGN PATENT DOCUMENTS

| | | |
|---|---|---|
| 401384 | 12/1990 | European Pat. Off. |
| WO 91/10470 | 7/1991 | WIPO. |
| 9526408 | 10/1995 | WIPO. |
| WO 95/26408 | 10/1995 | WIPO. |

OTHER PUBLICATIONS

Malik et al. (1992), 'Polyethylene Glycol (PEG)–modified Granulocyte–Macrophage Colony–stimulating Factor (GM–CSF) with Conserved Biological Activity', *Exp. Hematol.* 20:1028–1035.

Matheson et al. (1995), 'The In Vivo Responses of Neonatal Rat Dorsal Root Ganglion Neurons to Neurothrophins and GDNF', *Soc. Neurosci. Abstr.* 21:544.

Mullins et al. (1990), 'Ophthalmic Preparations', *Remington's Pharmaceutical Sciences*, 18th Ed, Ch. 86:1581–1595.

Nadol (1993), 'Hearing Loss', *New England J. of Medicine* 329:1092–1102.

Oppenheim et al. (1995), 'Developing motor neurons rescued from programmed and axotomy–induced cell death by GDNF', *Nature* 373:344–346.

Pirvola et al. (1992), 'Brain–derived neurotrophic factor and neurotrophin 3 mRNAs in the peripheral target fields of developing inner ear ganglia', *Proc. Natl. Acad. Sci. USA* 89:9915–9919.

Poulsen et al. (1994), 'TGFβ2 and TGFβ3 Are Potent Survival Factors for Midbrain Dopaminergic Neurons', *Neuron* 13:1245–1252.

Schecterson et al. (1994), 'Neurotrophin and neurotrophin receptor mRNA expression in developing inner ear', *Hearing Res.* 73:92–100.

Spoendlin (1984), 'Primary Neurons and Synapses', *Ultrastructural Atlas of the Inner Ear* Ch. 6:133–164.

Tresco et al. (1992), 'Polymer Encapsulated Neurotransmitter Secreting Cells', *ASAIO* 38:17–23.

Trupp et al. (1995), 'Peripheral Expression and Biological Activities of GDNF, a New Neurotrophic Factor for Avian and Mammalian Peripheral Neurons', *J. Cell Biol.* 130:137–148.

Wheeler et al. (1994), 'Expression of BDNF and NT–3 mRNA in hair cells of the organ of Corti: Quantitative analysis in developing rats', *Hearing Res.* 73:46–56.

Winn et al. (1991), 'Behavioral Recovery following Intrastriatal Implantation of Microencapsulated PC12 Cells', *Exper. Neurol.* 113:322–329.

Yan et al. (1992), 'Brain–derived neurotrophic factor rescues spinal motor neurons from axotomy–induced cell death', *Nature* 360:753–755.

Yan et al. (1995), 'In vivo neurotrophic effects of GDNF on neonatal and adult facial motor neurons', *Nature* 373:341–344.

Aebischer et al. (1991), 'Long–Term Cross–Species Brain Transplantation of a Polymer–Encapsulated Dopamine–Secreting Cell Line', *Exper. Neurol.* 111:269–275.

Apfel et al. (1991), 'Nerve Growth Factor Prevents Toxic Neuropathy in Mice', *Ann. Neurol.* 29:87–90.

Cunningham and Wells (1989), 'High–Resolution Epitope Mapping of hGH–Receptor Interactions by Alanine–Scanning Mutagenesis', *Science* 244:1081–1085.

Ernfors et al. (1995), 'Complementary Roles of BDNF and NT–3 in Vestibular Auditory Development', *Neuron* 14:1153–1164.

Gao et al. (1995), 'Neurotrophin–4/5 Enhances Survival of Cultured Spiral Ganglion Neurons and Protects Them from Cisplatin Neurotoxicity', *J. Neurosci.* 15(7):5079–5087.

Hefti (1986), 'Nerve Growth Factor Promotes Survival of Septal Cholinergic Neurons After Fimbrial Transections', *Neurosci.* 6:2155–2162.

(List continued on next page.)

*Primary Examiner*—Bruce R. Campell
*Assistant Examiner*—Anne-Marie Baker
*Attorney, Agent, or Firm*—Steven M. Odre; Ron K. Levy; Daniel R. Curry

[57] ABSTRACT

The present invention relates generally to methods for preventing and/or treating injury or degeneration of cochlear (and vestibular) hair cells and spiral ganglion neurons (as well as vestibular neurons—Carpa's neurons) by administering glial cell line-derived neurotrophic factor (GDNF). The invention relates more specifically to methods for treating sensorineural hearing loss and vestibular disorders.

20 Claims, 3 Drawing Sheets

OTHER PUBLICATIONS

Hefti (1994), 'Neurotrophic Factor Therapy for Nervous System Degenerative Diseases', *J. Neurobiol.* 25:1418–1435.

Hyman et al. (1991), 'BDNF is a neurotrophic factor for dopaminergic neurons of the substantia nigra', *Nature* 350:230–232.

Knusel et al. (1992), 'Brain–derived Neurotrophic Factor Administration Protects Basal Forebrain Cholinergic but Not Nigral Deopaminergic Neurons from Degenerative Changes after Axotomy in the Adult Rat Brain', *J. Neurosci.* 12(11):4391–4402.

Koliatsos et al. (1993), 'Evidence That Brain–Derived Neurotrophic Factor Is a Trophic Factor for Motor Neurons In Vivo', *Neuron* 10:359–367.

Korsching (1993), 'The Neurotrophic Factor Concept: A Reexamination', *J. Neurosci.* 13(7):2739–2748.

Krieglstein et al. (1995), 'TGF–β superfamily members promote survival of midbrain dopaminergic neurons and protect them against MPP$^+$ toxicity', *EMBO J.* 14:736–742.

Lefebrve et al. (1994), 'Neurotrophins affect survival and neuritogenesis by adult injured auditory neurons in vitro', *NeuroReport* 5:865–868.

Lin et al. (1993), 'GDNF: A Glial Cell Line–Derived Neurotrophic Factor for Midbrain Dopaminergic Neurons', *Science* 260:1130–1132.

Staecker, et al. (1995) 'NT–3 combined with CNTF promotes survival of neurons in modiolus–spiral ganglion explants', *Neuroreport*, 6(11):1533–1537.

Zheng, et al. (1995) 'Neurotrophin–4/5, Brain–Derived Neurotrophic Factor, and Neurotrophin–3 Promote Survival of Cultured Vestibular Ganglion Neurons and Protect Them against Neurotoxicity of Ototoxins', *J of Neurobiology,* 18(3):330–340.

Kelley (1997), 'Cellular Commitment and Differentiation in the Cochlea: Potential Advances Using Gene Transfer' *Audiol. Neurootol.* 2:50–60.

Lindner et al. (1995), 'Implantation of Encapsulated Catecholamine and GDNF–Producing Cells in Rats with Unilateral Dopamine Depletions and Parkinsonian Symptoms' *Exp. Neuro* 132:62–76.

Choi–Lundberg et al. (1997), 'Dopaminergic Neurons Protected from Degeneration by GDNF Gene Therapy' *Science* 275:838–841.

Raphael et al. (1996), 'Adenoviral–mediated gene transfer into guinea pig cochlear cells in vivo' *Neuro Ltrs* 207:137–141.

Weiss et al. (1997), 'Viral–Mediated Gene Transfer in the Cochlea' *Int. J. Devl Neuroscience* 4/5:577–583.

E. Marshall (1995) Science 269:1050–1055.

Ville et al (1995) Targeted Gene Therapy 9:190–199.

Figure 1

Mature Human GDNF

| | | | | | | | | | | | | |
|---|---|---|---|---|---|---|---|---|---|---|---|---|
| TCA | CCA | GAT | AAA | CAA | ATG | GCA | GTG | CTT | CCT | AGA | AGA | GAG | CGG | AAT |
| Ser | Pro | Asp | Lys | Gln | Met | Ala | Val | Leu | Pro | Arg | Arg | Glu | Arg | Asn |
| | | | | 5 | | | | | 10 | | | | | 15 |

```
TCA CCA GAT AAA CAA ATG GCA GTG CTT CCT AGA AGA GAG CGG AAT
Ser Pro Asp Lys Gln Met Ala Val Leu Pro Arg Arg Glu Arg Asn
              5                   10                      15

CGG CAG GCT GCA GCT GCC AAC CCA GAG AAT TCC AGA GGA AAA GGT
Arg Gln Ala Ala Ala Ala Asn Pro Glu Asn Ser Arg Gly Lys Gly
              20                  25                      30

CGG AGA GGC CAG AGG GGC AAA AAC CGG GGT TGT GTC TTA ACT GCA
Arg Arg Gly Gln Arg Gly Lys Asn Arg Gly Cys Val Leu Thr Ala
              35                  40                      45

ATA CAT TTA AAT GTC ACT GAC TTG GGT CTG GGC TAT GAA ACC AAG
Ile His Leu Asn Val Thr Asp Leu Gly Leu Gly Tyr Glu Thr Lys
              50                  55                      60

GAG GAA CTG ATT TTT AGG TAC TGC AGC GGC TCT TGC GAT GCA GCT
Glu Glu Leu Ile Phe Arg Tyr Cys Ser Gly Ser Cys Asp Ala Ala
              65                  70                      75

GAG ACA ACG TAC GAC AAA ATA TTG AAA AAC TTA TCC AGA AAT AGA
Glu Thr Thr Tyr Asp Lys Ile Leu Lys Asn Leu Ser Arg Asn Arg
              80                  85                      90

AGG CTG GTG AGT GAC AAA GTA GGG CAG GCA TGT TGC AGA CCC ATC
Arg Leu Val Ser Asp Lys Val Gly Gln Ala Cys Cys Arg Pro Ile
              95                  100                     105

GCC TTT GAT GAT GAC CTG TCG TTT TTA GAT GAT AAC CTG GTT TAC
Ala Phe Asp Asp Asp Leu Ser Phe Leu Asp Asp Asn Leu Val Tyr
              110                 115                     120

CAT ATT CTA AGA AAG CAT TCC GCT AAA AGG TGT GGA TGT ATC
His Ile Leu Arg Lys His Ser Ala Lys Arg Cys Gly Cys Ile
              125                 130
```

METHOD FOR PREVENTING AND TREATING SENSORINEURAL HEARING LOSS AND VESTIBULAR DISORDERS USING GLIAL CELL LINE-DERIVED NEUROTROPHIC FACTOR(GDNF) PROTEIN PRODUCT

CROSS-REFERENCES

This application is a continuation-in-part of U.S. Ser. No. 08/606,176, filed Feb. 23, 1996, now U.S. Pat. No. 5,837,681.

BACKGROUND OF THE INVENTION

The present invention relates generally to methods for preventing and/or treating injury or degeneration of inner ear sensory cells, such as hair cells and auditory neurons, by administering glial cell line-derived neurotrophic factor (GDNF) protein product. The invention relates specifically to methods for preventing and/or treating hearing loss due to variety of causes.

Neurotrophic factors are natural proteins, found in the nervous system or in non-nerve tissues innervated by the nervous system, that function to promote the survival and maintain the phenotypic differentiation of certain nerve and/or glial cell populations (Varon et al., Ann. Rev. Neuroscience, 1:327, 1979; Thoenen et al., Science, 229:238, 1985). Because of this physiological role, neurotrophic factors are useful in treating the degeneration of such nerve cells and the loss of differentiated function that results from nerve damage. Nerve damage is caused by conditions that compromise the survival and/or proper function of one or more types of nerve cells, including: (1) physical injury, which causes the degeneration of the axonal processes (which in turn causes nerve cell death) and/or nerve cell bodies near the site of injury, (2) temporary or permanent cessation of blood flow (ischemia) to parts of the nervous system, as in stroke, (3) intentional or accidental exposure to neurotoxins, such as the cancer and AIDS chemotherapeutic agents cisplatinum and dideoxycytidine, respectively, (4) chronic metabolic diseases, such as diabetes or renal dysfunction, or (5) neurodegenerative diseases such as Parkinson's disease, Alzheimer's disease, and Amyotrophic Lateral Sclerosis, which result from the degeneration of specific neuronal populations. In order for a particular neurotrophic factor to be potentially useful in treating nerve damage, the class or classes of damaged nerve cells must be responsive to the factor. It has been established that all neuron populations are not responsive to or equally affected by all neurotrophic factors.

The first neurotrophic factor to be identified was nerve growth factor (NGF). NGF is the first member of a defined family of trophic factors, called the neurotrophins, that currently includes brain-derived neurotrophic factor (BDNF), neurotrophin-3 (NT-3), NT-4/5, and NT-6 (Thoenen, Trends. Neurosci., 14:165–170, 1991; Snider, Cell, 77:627–638, 1994; Bothwell, Ann. Rev. Neurosci., 18:223–253, 1995). These neurotrophins are known to act via the family of trk tyrosine kinase receptors, i.e., trkA, trkB, trkC, and the low affinity p75 receptor (Snider, Cell, 77:627–638, 1994; Bothwell, Ann. Rev. Neurosci., 18:223–253, 1995; Chao et al., TINS 18:321–326, 1995).

Glial cell line-derived neurotrophic factor (GDNF) is a recently discovered protein identified and purified using assays based upon its efficacy in promoting the survival and stimulating the transmitter phenotype of mesencephalic dopaminergic neurons in vitro (Lin et al., Science, 260:1130–1132, 1993). GDNF is a glycosylated disulfide-bonded homodimer that has some structural homology to the transforming growth factor-beta (TGF-β) super family of proteins (Lin et al., Science, 260:1130–1132, 1993; Krieglstein et al., EMBO J., 14:736–742, 1995; Poulsen et al., Neuron, 13:1245–1252, 1994). GDNF mRNA has been detected in muscle and Schwann cells in the peripheral nervous system (Henderson et al., Science, 266:1062–1064, 1994; Trupp et al., J. Cell Biol., 130:137–148, 1995) and in type I astrocytes in the central nervous system (Schaar et al., Exp. Neurol., 124:368–371, 1993). In vivo, treatment with exogenous GDNF stimulates the dopaminergic phenotype of substantia nigra neurons and restores functional deficits induced by axotomy or dopaminergic neurotoxins in animal models of Parkinson's disease (Hudson et al., Brain Res. Bull., 36:425–432, 1995; Beck et al., Nature, 373:339–341, 1995; Tomac et al., Nature, 373:335–339, 1995; Hoffer et al., Neurosci. Lett., 182:107–111, 1994). Although originally thought to be relatively specific for dopaminergic neurons, at least in vitro, evidence is beginning to emerge indicating that GDNF may have a larger spectrum of neurotrophic targets besides mesencephalic dopaminergic and somatic motor neurons (Yan and Matheson, Nature 373:341–344, 1995; Oppenheim et al., Nature, 373:344–346, 1995; Matheson et al., Soc. Neurosci. Abstr, 21, 544, 1995; Trupp et al., J. Cell Biol., 130:137–148, 1995). In particular, GDNF was found to have neurotrophic efficacy on brainstem and spinal cord cholinergic motor neurons, both in vivo and in vitro (Oppenheim et al., Nature, 373:344–346, 1995; Zurn et al., Neuroreport, 6:113–118, 1994; Yan et al., Nature, 373:341–344, 1995; Henderson et al., Science, 266:1062–1064, 1994), on retinal neurons, such as photoreceptors in vitro (U.S. Pat. No. 5,641,750 by Louis, filed Nov. 29, 1995) and retinal ganglion cells both in vitro and in vivo (U.S. Pat. No. 5,641,750 by Yan, filed Nov. 29, 1995) and both in vitro and in vivo on sensory neurons from the dorsal root ganglion both (currently pending U.S. application Ser. No. 08/564, 844 (by Yan et al.) filed Nov. 29, 1995).

Of general interest to the present invention is WO 93/06116 (Lin et al., Syntex-Synergen Neuroscience Joint Venture), published Apr. 1, 1993, which reports that GDNF is useful for the treatment of nerve injury, including injury associated with Parkinson's disease. Also of interest are a report in Schmidt-Kastner et al., Mol. Brain Res., 26:325–330, 1994 that GDNF mRNA became detectable and was upregulated after pilocarpine-induced seizures; reports in Schaar et al., Exp. Neurol., 124:368–371, 1993 and Schaar et al., Exp. Neurol., 130:387–393, 1994 that basal forebrain astrocytes expressed moderate levels of GDNF mRNA under culture conditions, but that GDNF did not alter basal forebrain ChAT activity; and a report in U.S. Pat. No. 5,731,284 filed Sep. 28, 1995 that GDNF is useful for treating injury or degeneration of basal forebrain cholinergic neurons. GDNF has not previously been shown to promote survival, regeneration or protection against degeneration of inner ear cells such as hair cells and auditory neurons.

The neuroepithelial hair cells in the organ of Corti of the inner ear, transduce sound into neural activity, which is transmitted along the cochlear division of the eighth cranial nerve. This nerve consists of fibers from three types of neurons (Spoendlin, H. H. In: Friedmann, I. Ballantyne, J., eds. Ultrastructural Atlas of the Inner Ear; London, Butterworth, pp. 133–164, 1984): 1) afferent neurons, which lie in the spiral ganglion and connect the cochlea to the brainstem. 2) efferent olivocochlear neurons, which originate in the superior olivary complex and 3) autonomic adrenergic neurons, which originate in the cervical sympathetic trunk and innervate the cochlea. In the human, there are approximately 30,000 afferent cochlear neurons, with myelinated axons, each consisting of about 50 lamellae, and 4–6 μm in diameter. This histologic structure forms the basis of uniform conduction velocity, which is an important functional feature. Throughout the length of the auditory nerve, there is a trophic arrangement of afferent fibers, with 'basal' fibers wrapped over the centrally placed 'apical' fibers in a twisted rope-like fashion. Spoendlin (Spoendlin, H. H. In: Naunton, R. F., Fernadex, C. eds. Evoked Electrical Activity in the Auditory Nervous System. London, Academic Press, pp. 21–39, 1978) identified two types of afferent neurons in the spiral ganglion on the basis of morphologic differences: type I cells (95%) are bipolar and have myelinated cell bodies and axons that project to the inner hair cells. Type II cells (5%) are monopolar with unmyelinated axons and project to the outer hair cells of the organ of Corti. Each inner hair cell is innervated by about 20 fibers, each of which synapses on only one cell. In contrast, each outer hair cell is innervated by approximately six fibers, and each fiber branches to supply approximately 10 cells. Within the cochlea, the fibers divide into: 1) an inner spiral group, which arises primarily ipsilaterally and synapses with the afferent neurons to the inner hair cells, and 2) a more numerous outer radial group, which arises mainly contralaterally and synapses directly with outer hair cells. There is a minimal threshold at one frequency, the characteristic or best frequency, but the threshold rises sharply for frequencies above and below this level (Pickles, J. O. In: Introduction to the Physiology of Hearing. London, Academic Press, pp. 71–106, 1982). Single auditory nerve fibers therefore appear to behave as band-pass filters. The basilar membrane vibrates preferentially to different frequencies, at different distances along its length, and the frequency selectivity of each cochlear nerve fiber is similar to that of the inner hair cell to which the fiber is connected. Thus, each cochlear nerve fiber exhibits a turning curve covering a different range of frequencies from its neighboring fiber (Evans, E. F. In: Beagley H. A. ed. Auditory investigation: The Scientific and Technological basis. New York, Oxford University Press, 1979). By this mechanism, complex sounds are broken down into component frequencies (frequency resolution) by the filters of the inner ear.

Hearing loss of a degree sufficient to interfere with social and job-related communications is among the most common chronic neural impairments in the US population. On the basis of health-interview data (Vital and health statistics. Series 10. No. 176. Washington, D.C. (DHHS publication no. (PHS) 90-1504), it is estimated that approximately 4 percent of people under 45 years of age and about 29 percent of those 65 years or over have a handicapping loss of hearing. It has been estimated that more than 28 million Americans have hearing impairment and that as many as 2 million of this group are profoundly deaf (A report of the task force on the National Strategic plan. Bethesda, Md.: National Institute of Health, 1989). The prevalence of hearing loss increases dramatically with age. Approximately 1 per 1000 infants has a hearing loss sufficiently severe to prevent the unaided development of spoken language (Gentile, A. et al. Characteristics of persons with impaired hearing: United States, 1962–1963. Series 10. No. 35. Washington, D.C.: Government printing office, 1967 (DHHS publication no. (PHS) 1000) (Human communication and its disorders: an overview. Bethesda, Md.: National Institutes of health, 1970). More than 360 per 1000 persons over the age of 75 have a handicapping hearing loss (Vital and health statistics. Series 10. No. 176. Washington, D.C. (DHHS publication no. (PHS) 90-1504).

It has been estimated that the cost of lost productivity, special education, and medical treatment may exceed $30 billion per year for disorders of hearing, speech and language (1990 annual report of the National Deafness and other Communication Disorders Advisory Board. Washington, D.C.: Government Printing Office, 1991. (DHHS publication no. (NIH) 91-3189). The major common causes of profound deafness in childhood are genetic disorders and meningitis, constituting approximately 13 percent and 9 percent of the total, respectively (Hotchkiss, D. Demographic aspects of hearing impairment: questions and answers. 2nd ed. Washington, D.C.: Gallaudet University Press, 1989). In approximately 50 percent of the cases of childhood deafness, the cause is unknown, but is likely due to genetic causes or predisposition (Nance WE, Sweeney A. Otolaryngol. Clin. North Am 1975; 8: 19–48).

Impairment anywhere along the auditory pathway, from the external auditory canal to the central nervous system, may result in hearing loss. The auditory apparatus can be subdivided into the external and middle ear, inner ear and auditory nerve and central auditory pathways. Auditory information in humans is transduced from a mechanical signal to a neurally conducted electrical impulse by the action of approximately 15,000 neuroepithelial cells (hair cells) and 30,000 first-order neurons (spiral ganglion cells) in the inner ear. All central fibers of spiral ganglion neurons form synapses in the cochlear nucleus of the pontine brainstem. The number of neurons involved in hearing increases dramatically from the cochlea to the auditory brain stem and the auditory cortex. All auditory information is transduced by only 15,000 hair cells, of which the so-called inner hair cells, numbering 3500, are critically important, since they form synapses with approximately 90 percent of the 30,000 primary auditory neurons. Thus, damage to a relatively few cells in the auditory periphery can lead to substantial hearing loss. Hence, most causes of sensorineural loss can be ascribed to lesions in the inner ear (Nadol, J. B., New England Journal of Medicine, 1993, 329: 1092–1102).

Hearing loss can be on the level of conductivity, sensorineural and central level. Conductive hearing loss is caused by lesions involving the external or middle ear, resulting in the destruction of the normal pathway of airborne sound amplified by the tympanic membrane and the ossicles to the inner ear fluids. Sensorineural hearing loss is caused by lesions of the cochlea or the auditory division of the eight cranial nerve. Central hearing loss is due to lesions of the central auditory pathways. These consist of the cochlear and dorsal olivary nucleus complex, inferior colliculi, medial geniculate bodies, auditory cortex in the temporal lobes and interconnecting afferent and efferent fiber tracts (Adams R. D. and Maurice, V. Eds. in: Principles of Neurology. 1989. McGraw-Hill Information services Company. PP 226–246).

As mentioned previously, at least 50 percent of cases of profound deafness in childhood have genetic causes (Brown, K. S. Med. Clin. North AM. 1969; 53: 741–72). If one takes into consideration the probability that genetic predisposition is a major causative factor in presbycusis—or age-related hearing loss—which affects one third of the population over 75 years of age (Nadol, J. B. In: Beasley DS, Davis GA, eds. Aging: Communication Processes and Disorders. New York: Grune & Stratton, 1981:63–85), genetic and hereditary factors are probably the single most common cause of hearing loss. Genetic anomalies are much more commonly expressed as sensorineural hearing loss than as conductive hearing loss. Genetically determined sensorineural hearing loss is clearly a major, if not the main cause of sensorineural loss, particularly in children (Nance WE, Sweeney A. Otolaryngol. Clin. North Am 1975; 8: 19–48). Among the most common syndromal forms of sensorineural loss are Waardenburg's syndrome, Alport's syndrome and Usher's syndrome.

A variety of commonly used drugs have ototoxic properties. The best known are the aminoglycoside antibiotics (Lerner, S. A. et al eds. Aminoglycoside ototoxicity. Boston: Little, Brown, 1981; Smith, C. R. et al. N Engl. J. Med. 1980; 302: 1106–9), loop diuretics (Bosher, S. K., Acta Otolaryngol. (Stockh) 1980; 90: 4–54), salicylates (Myers, E. N. at al. N Engl. J. Med. 1965; 273:587–90) and antineoplastic agents such as cisplatin (Strauss, M. at al. Laryngoscope 1983; 143:1263–5). Ototoxicity has also been described during oral or parenteral administration of erythromycin (Kroboth, P. D. at al. Arch. Intern Med. 1983; 1:169–79; Achweitzer, V. G., Olson, N. Arch. Otolaryngol. 1984; 110:258–60).

Most ototoxic substances cause hearing loss by damaging the cochlea, particularly the auditory hair cells and the stria vascularis, a specialized epithelial organ within the inner ear, that is responsible for the homeostasis of fluids and electrolytes (Nadol, J. B. New England J. Med. 1993, 329: 1092–1102). Secondary neural degeneration may occur many years after an ototoxic event affecting the hair cells. There is evidence that some ototoxic substances may be selectively concentrated within the inner ear, resulting in progressive sensorineural loss despite the discontinuation of systemic administration (Federspil, P. at al. J. Infect. Dis. 1976; 134 Suppl: S200–S205)

Trauma due to acoustic overstimulation is another leading cause of deafness. There is individual susceptibility to trauma from noise. Clinically important sensorineural hearing loss may occur in some people exposed to high-intensity noise, even below levels approved by the Occupational Safety and Health Agency (Osguthorpe, J. D. ed. Washington D.C.: American Academy of Otolaryngology-Head and Neck Surgery Foundation, 1988).

Demyelinating processes, such as multiple sclerosis, may cause sensorineural hearing loss (Noffsinger, D at al. Acta Otolaryngol Suppl (Stockh) 1972; 303:1–63). More recently, a form of immune-mediated sensorineural hearing loss has been recognized (McCabe, B. F. Ann Otol Rhinol Laryngol 1979; 88:585–9). The hearing loss is usually bilateral, is rapidly progressive (measured in weeks and months), and may or may not be associated with vestibular symptoms.

A variety of tumors, both primary and metastatic, can produce either a conductive hearing loss, or a sensorineural hearing loss, by invading the inner ear or auditory nerve (Houck, J. R. et al. Otolaryngol Head Neck Surg 1992; 106:92–7). A variety of degenerative disorders of unknown cause can produce sensorineural hearing loss. Meniere's syndrome (Nadol, J. B. ed. Meniere's disease: pathogenesis, pathophysiology, diagnosis, and treatment. Amsterdam: Kugler & Ghedini 1989), characterized by fluctuating sensorineural hearing loss, episodic vertigo, and tinnitus, appears to be caused by a disorder of fluid homeostasis within the inner ear, although the pathogenesis remains unknown. Sudden idiopathic sensorineural hearing loss (Wilson, W. R. at al. Arch Otolaryngol 1980; 106:772–6), causing moderate-to-severe sensorineural deafness, may be due to various causes, including inner ear ischemia and viral labyrinthitis.

Presbycusis, the hearing loss associated with aging, affects more than one third of persons over the age of 75 years. The most common histopathological correlate of presbycusis is the loss of neuroepithelial (hair) cells, neurons, and the stria vascularis of the peripheral auditory system (Schuknecht H. F. Pathology of the Ear. Cambridge, Mass: Harvard University Press, 1974:388–403). Presbycusis is best understood as resulting from the cumulative effects of several noxious influences during life, including noise trauma, ototoxicity and genetically influenced degeneration.

Certain neurotrophic factors have been shown to regulate neuronal differentiation and survival during development (Korsching S. J. Neurosci. 13:2739–2748,1993) and to protect neurons from injury and toxins in adult (Hefti, Neurosci. 6:2155–2162, 1986; Apfel et al., Ann Neurol 29:87–89, 1991; Hyman et al., Nature 350:230–233, 1991; Knusel et al., J. Neurosci. 12:4391–4402, 1992; Yan et al., Nature, 360:753–755, 1992; Koliatsos et al., Neuron, 10:359–367, 1993). In situ hybridization studies indicate that mRNAs for the neurotrophin receptors TrkB and TrkC are expressed by developing cochleovestibular ganglia (Ylikoski et al., Hear. Res. 65:69–78 1993; Schecterson et al., Hearing Res. 73: 92–100 1994) and that mRNAs for BDNF and NT-3 are found in the inner ear, including the organ of Corti (Pirvola et al., Proc. Natl. Acad. Sci. USA 89: 9915–9919, 1992; Schecterson et al., Hearing Res. 73: 92–100 1994; Wheeler et al., Hearing Res. 73: 46–56, 1994). The physiological role of BDNF and NT-3 in the development of the vestibular and auditory systems was investigated in mice that carry a deleted BDNF and /or NT-3 gene (Ernfors et al., Neuron 14: 1153–1164 1995). In the cochlea, BDNF mutants lost type-2 spiral neurons, causing an absence of outer hair cell innervation. NT-3 mutants showed a paucity of afferents and lost 87 percent of spiral neurons, presumably corresponding to type-1 neurons, which innervate inner hair cells. Double mutants had an additive loss, lacking all vestibular and spiral neurons. The requirement of TrkB and TrkC receptors for the survival of specific neuronal populations and the maintenance of target innervation in the peripheral sensory system of the inner ear was demonstrated by studying mice carrying a germline mutation in the tyrosine kinase catalytic domain of these genes (Schimmang et al., Development, 121: 3381–3391 1995). Gao et al., (J. Neurosci. 15: 5079–5087, 1995) showed survival-promoting potency of NT-4/5, BDNF and NT-3 for rat postnatal spiral ganglion neurons in dissociated cultures and that NT-4/5 protected these neurons from neurotoxic effects of the anti-cancer drug, cisplatin. Also, BDNF and NT-3 have been shown to support the survival of adult rat auditory neurons in dissociated cultures (Lefébvre et al., NeuroReport 5: 865–868, 1994).

There have been no previous reports of the use of GDNF in the treatment of hearing loss. Since hearing impairment is a serious affliction, the identification of any agent and treatment method that can protect the auditory neurons and hair cells from damage would be of great benefit.

SUMMARY OF THE INVENTION

The present invention provides methods for treating sensorineural hearing loss comprising administering to a subject having a lesion in the inner ear a therapeutically effective amount of a glial cell line-derived neurotrophic factor (GDNF) protein product. For example, the hearing loss may be associated with injury or degeneration of neuroepithelial hair cells (cochlear hair cells) or spiral ganglion neurons in the inner ear.

The present invention is based on the discoveries that hair cells respond to GDNF by resisting the toxic effects of ototoxins, such as cisplatin and neomycin, and that auditory neurons also respond to GDNF by resisting the toxic effects of variety of ototoxins, such as for example cisplatin, neomycin, and sodium salicylate. Thus, a therapeutically effective amount of GDNF protein product may be administered to promote the protection, survival or regeneration of hair cells and spiral ganglion neurons.

It has also been discovered that lesions or disturbances to the vestibular apparatus may also be treated by administering to a subject having such a lesion or disturbance a therapeutically effective amount of a GDNF protein product. Such lesions may result in dizziness, vertigo or loss of balance.

It is contemplated that such GDNF protein products would include a GDNF protein such as that depicted by the amino acid sequence set forth in FIG. 1 (SEQ ID NO: 1), as well as variants and derivatives thereof. It is also contemplated that such GDNF protein products would include [Met$^{-1}$]GDNF.

According to the invention, the GDNF protein product may be administered parenterally at a dose ranging from about 1 µg/kg/day to about 100 mg/kg/day, typically at a dose of about 0.1 mg/kg/day to about 25 mg/kg/day, and usually at a dose of about 5 mg/kg/day to about 20 mg/kg/day. It is also contemplated that, depending on the individual patient's needs and route of administration, the GDNF protein product may be given at a lower frequency such as weekly or several times per week, rather than daily. It is further contemplated that GDNF protein product may be administered directly into the middle ear or the inner ear. One skilled in the art will appreciate that with such administration of a smaller amount of GDNF protein product may be used, for example, a direct middle ear or inner-ear administration dose in the range of about 1 µg/ear to about 1 mg/ear in a single injection or in multiple injections.

It is further contemplated that GDNF protein product be administered in combination or conjunction with an effective amount of a second therapeutic agents, such as BDNF and NT-3. The invention also provides for the use of GDNF protein product in the manufacture of a medicament or pharmaceutical composition for the treatment of injury or degeneration of hair cells and auditory neurons for the variety of causes of sensorineural hearing loss. Such pharmaceutical compositions include topical, oral or middle and inner ear GDNF protein product formulations or in combination with cochlear implants.

It will also be appreciated by those skilled in the art that the administration process can be accomplished via cell therapy and gene therapy means, as further described below. For example, in a gene therapy means cells have been modified to produce and secrete the GDNF protein product. The cells may be modified ex vivo or in vivo. Numerous additional aspects and advantages of the invention will become apparent to those skilled in the art upon consideration of the following detailed description of the invention which describes presently preferred embodiments thereof.

BRIEF DESCRIPTION OF THE DRAWINGS

FIG. 1 (SEQ ID NO: 1) depicts an amino acid sequence of a glial cell line-derived neurotrophic factor (GDNF) protein product, i.e., human GDNF.

DETAILED DESCRIPTION OF THE INVENTION

Figure 2:
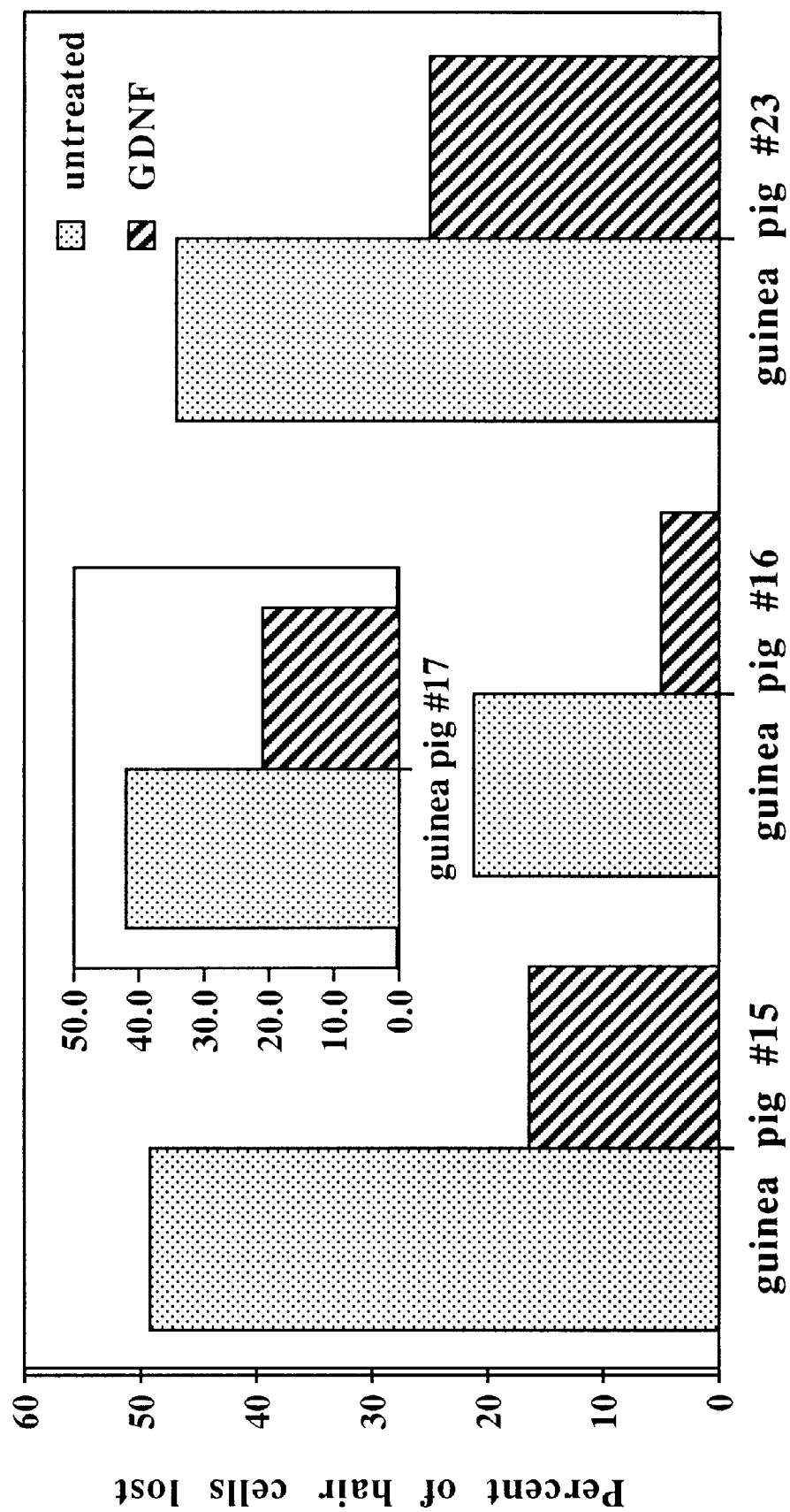
FIG. 2 depicts the results of the study described in Example 3 wherein a GDNF protein product is shown to protect cochlear hair cells against ototoxicity in an animal model.

The present invention provides a method for preventing and/or treating sensorineural hearing loss by administering a therapeutically effective amount of glial cell line-derived neurotrophic factor (GDNF) protein product. According to one aspect of the invention, methods are provided for treating damaged hair cells and auditory neurons by administering a therapeutically effective amount of GDNF protein product by means of a pharmaceutical composition, the implantation of GDNF-expressing cells, or GDNF gene therapy. The invention may be practiced using any biologically active GDNF protein product, including a GDNF protein represented by the amino acid sequence set forth in SEQ ID NO: 1, including variants and derivatives thereof. In addition to oral, parenteral or topical delivery of the GDNF protein product, administration via cell therapy and gene therapy procedures is contemplated.

The present invention is based on the initial discoveries that GDNF protects hair cells from ototoxins-induced cell death in explant cultures of rat's cochlea and dissociated spiral ganglion neurons from adult rat in culture. It is contemplated that administration of exogenous GDNF protein product will protect hair cells and spiral ganglion neurons from traumatic damage (such as noise trauma and acute or chronic treatments of cisplatin and aminoglycoside antibiotics) or from damage resulting from a lack of neurotrophic factors caused by interruption of transport of the factors from the axon to the cell body. Such treatment is expected to allow hair cells and /or auditory neurons to tolerate intermittent insults from either environmental noise trauma, treatments with ototoxins and to slow down the progressive degeneration of the auditory neurons and hair cells, that is responsible for hearing loss in pathological conditions such as presbycusis (age-related hearing loss), inherited sensorineural degeneration, and post-idiopathic hearing losses and to preserve the functional integrity of the inner ear. It will also support the auditory neurons for a better and longer performance of cochlear implants.

According to the invention, the GDNF protein product may be administered into the middle ear at a dose ranging from about 1 µg/kg/day to about 100 mg/kg/day, typically at a dose of about 0.1 mg/kg/day to about 25 mg/kg/day, and usually at a dose of about 5 mg/kg/day to about 20 mg/kg/day. GDNF protein product may be administered directly into the inner ear in cases where invasion of the inner ear is already in place such as in the procedure of cochlear implant or surgeries of the inner ear. In such cases, a smaller amount of GDNF protein product will be administered, for example, from about 1 µg/ear to about 1 mg/ear in a single injection or in multiple injections. In cases where a chronic administration of the factor is needed, an Alzet mini-pump will be placed attached to a cannula the tip of which will be introduced into the middle or inner ear for a continuous release of the factor. GDNF can be also developed in a form of ear-drops which will penetrate the tympanic membrane of the Bulla. It is further contemplated that GDNF protein product be administered with an effective amount of a second therapeutic agent for the treatment of auditory neuron degeneration, together with BDNF and NT-3 as well as other factors or drugs used currently or in the future for the treatment of the various inner ear pathologies. A variety of pharmaceutical formulations and different delivery techniques are described in further detail below.

As used herein, the term "GDNF protein product" includes purified natural, synthetic or recombinant glial cell line-derived neurotrophic factor, biologically active GDNF variants (including insertion, substitution and deletion variants), and chemically modified derivatives thereof. Also included are GDNFs that are substantially homologous to the human GDNF having the amino acid sequence set forth in SEQ ID NO: 1. GDNF protein products may exist as homodimers or heterodimers in their biologically active form.

The term "biologically active" as used herein means that the GDNF protein product demonstrates similar neurotrophic properties, but not necessarily all of the same properties, and not necessarily to the same degree, as the GDNF having the amino acid sequence set forth in SEQ ID NO: 1. The selection of the particular neurotrophic properties of interest depends upon the use for which the GDNF protein product is being administered.

The term "substantially homologous" as used herein means having a degree of homology to the GDNF having the amino acid sequence set forth in SEQ ID NO: 1 that is preferably in excess of 70%, most preferably in excess of 80%, and even more preferably in excess of 90% or 95%. For example, the degree of homology between the rat and the human protein is about 93%, and it is contemplated that preferred mammalian GDNF will have a similarly high degree of homology. The percentage of homology as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972), the disclosure of which is hereby incorporated by reference). Preferably the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any GDNF protein product which may be isolated by virtue of cross-reactivity with antibodies to the GDNF of SEQ ID NO: 1 or whose genes may be isolated through hybridization with the gene or with segments of the gene encoding the GDNF of SEQ ID NO: 1.

The GDNF protein products according to this invention may be isolated or generated by any means known to those skilled in the art. Exemplary methods for producing GDNF protein products useful in the present invention are described in U.S. application Ser. No. 08/182,183 filed May 23, 1994 and its parent applications; PCT Application No. PCT/US92/07488 filed Sep. 17, 1992, published as WO 93/06116 (Lin et al., Syntex-Synergen Neuroscience Joint Venture); European Patent Application No. 92921022.7, published as EP 610 254; and co-owned, co-pending U.S. application Ser. No. 08/535,681 filed Sep. 28, 1995 ("Truncated Glial Cell-Line Derived Neurotrophic Factor"), the disclosures of which are hereby incorporated by reference.

Naturally-occurring GDNF protein products may be isolated from mammalian neuronal cell preparations, or from a mammalian cell line secreting or expressing GDNF. For example, WO 93/06116 describes the isolation of GDNF from serum-free growth conditioned medium of B49 glioblastoma cells. GDNF protein products may also be chemically synthesized by any means known to those skilled in the art. GDNF protein products are preferably produced via recombinant techniques because they are capable of achieving comparatively higher amounts of protein at greater purity. Recombinant GDNF protein product forms include glycosylated and non-glycosylated forms of the protein, and protein expressed in bacterial, mammalian or insect cell systems.

In general, recombinant techniques involve isolating the genes responsible for coding GDNF, cloning the gene in suitable vectors and cell types, modifying the gene if necessary to encode a desired variant, and expressing the gene in order to produce the GDNF protein product. Alternatively, a nucleotide sequence encoding the desired GDNF protein product may be chemically synthesized. It is contemplated that GDNF protein product may be expressed using nucleotide sequences which differ in codon usage due to the degeneracies of the genetic code or allelic variations. WO 93/06116 describes the isolation and sequencing of a cDNA clone of the rat GDNF gene, and the isolation, sequencing and expression of a genomic DNA clone of the human GDNF gene. WO 93/06116 also describes vectors, host cells, and culture growth conditions for the expression of GDNF protein product. Additional vectors suitable for the expression of GDNF protein product in E. coli are disclosed in published European Patent Application No. EP 0 423 980 ("Stem Cell Factor") published Apr. 24, 1991, the disclosure of which is hereby incorporated by reference. The DNA sequence of the gene coding for mature human GDNF and the amino acid sequence of the GDNF is shown in FIG. 19 (SEQ ID NO: 5) of WO 93/06116. FIG. 19 does not show the entire coding sequence for the pre-pro portion of GDNF, but the first 50 amino acids of human pre-pro GDNF are shown in FIG. 22 (SEQ ID NO: 8) of WO 93/06116.

Naturally-occurring GDNF is a disulfide-bonded dimer in its biologically active form. The material isolated after expression in a bacterial system is essentially biologically inactive, and exists as a monomer. Refolding is necessary to produce the biologically active disulfide-bonded dimer. Processes for the refolding and maturation of the GDNF expressed in bacterial systems are described in WO 93/06116. Standard in vitro assays for the determination of GDNF activity are described in WO 93/06116 and in co-owned, co-pending U.S. application Ser. No. 08/535,681 filed Sep. 28, 1995, and are hereby incorporated by reference.

A. GDNF variants

The term "GDNF variants" as used herein includes polypeptides in which amino acids have been deleted from ("deletion variants"), inserted into ("addition variants"), or substituted for ("substitution variants"), residues within the amino acid sequence of naturally-occurring GDNF. Such variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made provided that the final molecule possesses GDNF biological activity.

Mutagenesis techniques for the replacement, insertion or deletion of one or more selected amino acid residues are well known to one skilled in the art (e.g., U.S. Pat. No. 4,518,584, the disclosure of which is hereby incorporated by reference.) There are two principal variables in the construction of variants: the location of the mutation site and the nature of the mutation. In designing GDNF variants, the selection of the mutation site and nature of the mutation will depend on the GDNF characteristic(s) to be modified. The sites for mutation can be modified individually or in series, e.g., by (1) substituting first with conservative amino acid choices and then with more radical selections depending upon the results achieved, (2) deleting the target amino acid residue, or (3) inserting amino acid residues adjacent to the located site. Conservative changes in from 1 to 20 amino acids are preferred. Once the amino acid sequence of the desired GDNF protein product is determined, the nucleic acid sequence to be used in the expression of the protein is readily determined. N-terminal and C-terminal deletion variants may also be generated by proteolytic enzymes.

For GDNF deletion variants, deletions generally range from about 1 to 30 residues, more usually from about 1 to 10 residues, and typically from about 1 to 5 contiguous residues. N-terminal, C-terminal and internal intrasequence deletions are contemplated. Deletions may be introduced into regions of low homology with other TGF-β super family members to modify the activity of GDNF. Deletions in areas of substantial homology with other TGF-β super family sequences will be more likely to modify the GDNF biological activity more significantly. The number of consecutive deletions will be selected so as to preserve the tertiary structure of the GDNF protein product in the affected domain, e.g., cysteine crosslinking. Non-limiting examples of deletion variants include truncated GDNF protein products lacking from one to forty N-terminal amino acids of GDNF, or variants lacking the C-terminal residue of GDNF, or combinations thereof, as described in co-owned, co-pending U.S. application Ser. No. 08/535,681 filed Sep. 28, 1995, which is hereby incorporated by reference.

For GDNF addition variants, amino acid sequence additions typically include N-and/or C-terminal fusions ranging in length from one residue to polypeptides containing a hundred or more residues, as well as internal intrasequence additions of single or multiple amino acid residues. Internal additions may range generally from about 1 to 10 residues, more typically from about 1 to 5 residues, and usually from about 1 to 3 amino acid residues. Examples of N-terminal addition variants include GDNF with an N-terminal methionyl residue (an artifact of the direct expression of GDNF in bacterial recombinant cell culture), which is designated [Met$^{-1}$]GDNF, and fusion of a heterologous N-terminal signal sequence to the N-terminus of GDNF to facilitate the secretion of mature GDNF from recombinant host cells. Such signal sequences generally will be obtained from, and thus be homologous to, the intended host cell species. Additions may also include amino acid sequences derived from the sequence of other neurotrophic factors. A preferred GDNF protein product for use according to the present invention is the recombinant human [Met$^{-1}$]GDNF.

GDNF substitution variants have at least one amino acid residue of the GDNF amino acid sequence removed and a different residue inserted in its place. Such substitution variants include allelic variants, which are characterized by naturally-occurring nucleotide sequence changes in the species population that may or may not result in an amino acid change. Examples of substitution variants (see, e.g., SEQ ID NO: 50) are disclosed in co-owned, co-pending U.S. application Ser. No. 08/535,681 filed Sep. 28, 1995, and are hereby incorporated by reference.

Specific mutations of the GDNF amino acid sequence may involve modifications to a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of an 0-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) result in non-glycosylation at the modified tripeptide sequence. Thus, the expression of appropriate altered nucleotide sequences produces variants which are not glycosylated at that site. Alternatively, the GDNF amino acid sequence may be modified to add glycosylation sites.

One method for identifying GDNF amino acid residues or regions for mutagenesis is called "alanine scanning mutagenesis" as described by Cunningham and Wells (*Science*, 244:1081–1085, 1989). In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed GDNF variants are screened for the optimal combination of desired activity and degree of activity.

The sites of greatest interest for substitutional mutagenesis include sites where the amino acids found in GDNF proteins from various species are substantially different in terms of side-chain bulk, charge, and/or hydrophobicity. Other sites of interest are those in which particular residues of GDNF-like proteins, obtained from various species, are identical. Such positions are generally important for the biological activity of a protein. Initially, these sites are substituted in a relatively conservative manner. Such conservative substitutions are shown in Table 1 under the heading of preferred substitutions. If such substitutions result in a change in biological activity, then more substantial changes (exemplary substitutions) are introduced, and/or other additions or deletions may be made, and the resulting products screened for activity.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |

TABLE 1-continued

Amino Acid Substitutions

| Original Residue | Preferred Substitutions | Exemplary Substitutions |
|---|---|---|
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

Conservative modifications to the amino acid sequence (and the corresponding modifications to the encoding nucleic acid sequences) are expected to produce GDNF protein products having functional and chemical characteristics similar to those of natural GDNF. In contrast, substantial modifications in the functional and/or chemical characteristics of GDNF protein products may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for another. Such substituted residues may be introduced into regions of the GDNF protein that are homologous with other TGF-β super family proteins, or into the non-homologous regions of the molecule.

B. GDNF Derivatives

Chemically modified derivatives of GDNF or GDNF variants may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or, further formulated for oral, pulmonary or other delivery routes), and determining its effectiveness.

Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water.

The polymer may be of any molecular weight, and may be branched or unbranched. For polyethylene glycol, the preferred molecular weight ranges from about 2 kDa to about 100 kDa for ease in handling and manufacturing (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of polyethylene glycol on a therapeutic protein or variant).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to protein (or peptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono-, di-, tri-, etc.), the molecular weight of the polymer selected, whether the polymer is branched or unbranched, and the reaction conditions.

The polyethylene glycol molecules (or other chemical moieties) should be attached to the protein with consideration of effects on functional or antigenic domains of the protein. There are a number of attachment methods available to those skilled in the art. See for example, EP 0 401 384, the disclosure of which is hereby incorporated by reference (coupling PEG to G-CSF), see also Malik et al., *Exp. Hematol.*, 20:1028–1035, 1992 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching the polyethylene glycol molecule(s). For therapeutic purposes, attachment at an amino group, such as attachment at the N-terminus or lysine group is preferred. Attachment at residues important for receptor binding should be avoided if receptor binding is desired.

One may specifically desire an N-terminal chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at a pH which allows one to take advantage of the pKa differences between the e-amino group of the lysine residues and that of the a-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol propionaldehyde, containing a single reactive aldehyde, may be used.

The present invention contemplates use of derivatives which are prokaryote-expressed GDNF, or variants thereof, linked to at least one polyethylene glycol molecule, as well as use of GDNF, or variants thereof, attached to one or more polyethylene glycol molecules via an acyl or alkyl linkage.

Pegylation may be carried out by any of the pegylation reactions known in the art. See, for example: *Focus on Growth Factors,* 3 (2) :4–10, 1992; EP 0 154 316, the disclosure of which is hereby incorporated by reference; EP 0 401 384; and the other publications cited herein that relate to pegylation. The pegylation may be carried out via an acylation reaction or an alkylation reaction with a reactive polyethylene glycol molecule (or an analogous reactive water-soluble polymer).

Pegylation by acylation generally involves reacting an active ester derivative of polyethylene glycol with the GDNF protein or variant. Any known or subsequently discovered reactive PEG molecule may be used to carry out the pegylation of GDNF protein or variant. A preferred activated PEG ester is PEG esterified to N-hydroxysuccinimide. As used herein, "acylation" is contemplated to include without limitation the following types of linkages between the therapeutic protein and a water soluble polymer such as PEG: amide, carbamate, urethane, and the like. See *Bioconjugate Chem.,* 5:133–140, 1994. Reaction conditions may be selected from any of those known in the pegylation art or those subsequently developed, but should avoid conditions of temperature, solvent, and pH that would inactivate the GDNF or variant to be modified.

Pegylation by acylation will generally result in a poly-pegylated GDNF protein or variant. Preferably, the connecting linkage will be an amide. Also preferably, the resulting product will be substantially only (e.g., >95%) mono-, di- or tri-pegylated. However, some species with higher degrees of pegylation may be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with the GDNF protein or variant in the presence of a reducing agent. Pegylation by alkylation can also result in poly-pegylated GDNF protein or variant. In addition, one can manipulate the reaction conditions to favor pegylation substantially only at the a-amino group of the N-terminus of the GDNF protein or variant (i.e., a mono-pegylated protein). In either case of monopegylation or polypegylation, the PEG groups are preferably attached to the protein via a —$CH_2$—NH— group. With particular reference to the —$CH_2$— group, this type of linkage is referred to herein as an "alkyl" linkage.

Derivatization via reductive alkylation to produce a monopegylated product exploits differential reactivity of different types of primary amino groups (lysine versus the N-terminal) available for derivatization. The reaction is performed at a pH which allows one to take advantage of the pKa differences between the e-amino groups of the lysine residues and that of the a-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention contemplates use of a substantially homogeneous preparation of monopolymer/GDNF protein (or variant) conjugate molecules (meaning GDNF protein or variant to which a polymer molecule has been attached substantially only (i.e., >95%) in a single location). More specifically, if polyethylene glycol is used, the present invention also encompasses use of pegylated GDNF protein or variant lacking possibly antigenic linking groups, and having the polyethylene glycol molecule directly coupled to the GDNF protein or variant.

Thus, it is contemplated that GDNF protein products to be used in accordance with the present invention may include pegylated GDNF protein or variants, wherein the PEG group(s) is (are) attached via acyl or alkyl groups. As discussed above, such products may be mono-pegylated or poly-pegylated (e.g., containing 2–6, and preferably 2–5, PEG groups). The PEG groups are generally attached to the protein at the a- or e-amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol. As used herein, polyethylene glycol is meant to encompass any of the forms of PEG that have been used to derivatize other proteins, such as mono-(C1–C10) alkoxy- or aryloxy-polyethylene glycol.

In general, chemical derivatization may be performed under any suitable condition used to react a biologically active substance with an activated polymer molecule. Methods for preparing pegylated GDNF protein or variant will generally comprise the steps of (a) reacting a GDNF protein or variant with polyethylene glycol (such as a reactive ester or aldehyde derivative of PEG) under conditions whereby the protein becomes attached to one or more PEG groups, and (b) obtaining the reaction product(s). In general, the optimal reaction conditions for the acylation reactions will be determined case-by-case based on known parameters and the desired result. For example, the larger the ratio of PEG:protein, the greater the percentage of poly-pegylated product.

Reductive alkylation to produce a substantially homogeneous population of mono-polymer/GDNF protein (or variant) conjugate molecule will generally comprise the steps of: (a) reacting a GDNF protein or variant with a reactive PEG molecule under reductive alkylation conditions, at a pH suitable to permit selective modification of the a-amino group at the amino terminus of said GDNF protein or variant; and (b) obtaining the reaction product(s).

For a substantially homogeneous population of mono-polymer/GDNF protein (or variant) conjugate molecules, the reductive alkylation reaction conditions are those which permit the selective attachment of the water soluble polymer moiety to the N-terminus of GDNF protein or variant. Such reaction conditions generally provide for pKa differences between the lysine amino groups and the a-amino group at the N-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal a-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa. The preferred average molecular weight is about 5 kDa to about 50 kDa, particularly preferably about 12 kDa to about 25 kDa. The ratio of water-soluble polymer to GDNF protein or variant will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any GDNF protein or variant having an a-amino group at the amino terminus, and provide for a substantially homogenous preparation of monopolymer/GDNF protein (or variant) conjugate. The term "monopolymer/GDNF protein (or variant) conjugate" is used here to mean a composition comprised of a single polymer molecule attached to a molecule of GDNF protein or GDNF variant protein. The monopolymer/GDNF protein (or variant) conjugate preferably will have a polymer molecule located at the N-terminus, but not on lysine amino side groups. The preparation will preferably be greater than 90% monopolymer/GDNF protein (or variant) conjugate, and more preferably greater than 95% monopolymer/GDNF protein (or variant) conjugate, with the remainder of observable molecules being unreacted (i.e., protein lacking the polymer moiety).

For the present reductive alkylation, the reducing agent should be stable in aqueous solution and preferably be able to reduce only the Schiff base formed in the initial process of reductive alkylation. Preferred reducing agents may be selected from sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on the published information relating to derivatization of proteins with water soluble polymers (see the publications cited herein).

C. GDNF Protein Product Pharmaceutical Compositions

GDNF protein product pharmaceutical compositions typically include a therapeutically effective amount of a GDNF protein product in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial perilymph, possibly supplemented with other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the rate of release of GDNF protein product, or for promoting the absorption or penetration of GDNF protein product across the tympanic membrane. Such excipients are those substances usually and customarily employed to formulate dosages for middle-ear administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulations will be determined by one skilled in the art depending upon considerations such as the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the present GDNF proteins, variants and derivatives.

Other effective administration forms, such as middle-ear slow-release formulations, inhalant mists, or orally active formulations are also envisioned. For example, in a sustained release formulation, the GDNF protein product may be bound to or incorporated into particulate preparations of polymeric compounds (such as polylactic acid, polyglycolic acid, etc.) or liposomes. Hylauronic acid may also be used, and this may have the effect of promoting sustained duration in the circulation. The GDNF protein product pharmaceutical composition also may be formulated for middle-ear administration, e.g., by tympanic membrane infusion or injection, and may also include slow-release or sustained circulation formulations. Such middle-ear administered therapeutic compositions are typically in the form of a pyrogen-free, middle-ear acceptable aqueous solution comprising the GDNF protein product in a pharmaceutically acceptable vehicle. One preferred vehicle is sterile distilled water.

It is also contemplated that certain formulations containing GDNF protein product are to be administered orally. GDNF protein product which is administered in this fashion may be encapsulated and may be formulated with or without those carriers customarily used in the compounding of solid dosage forms. The capsule may be designed to release the active portion of the formulation at the point in the gastrointestinal tract when bioavailability is maximized and pre-systemic degradation is minimized. Additional excipients may be included to facilitate absorption of GDNF protein product. Diluents, flavorings, low melting point waxes, vegetable oils, lubricants, suspending agents, tablet disintegrating agents, and binders may also be employed.

The formulation of topical ear preparations, including middle-ear solutions, suspensions and ointments is well known to those skilled in the art (see Remington's Pharmaceutical Sciences, 18th Edition, Chapter 86, pages 1581–1592, Mack Publishing Company, 1990). Other modes of administration are available, including injections to the middle ear, and methods and means for producing middle-ear preparations suitable for such modes of administration are also well known.

As used in this application, "middle-ear" refers to the space between the tympanic membrane and the inner ear. This location is external to all inner ear tissue and an invasive procedure might not be required to access this region if a formulation will be developed so that the GDNF will penetrate through the tympanic membrane. Otherwise, the material will be introduced to the middle ear by injection through the tympanic membrane or, in case repeated administrations are needed, a hole will be made in the tympanic membrane. Examples of such systems include inserts and "topically" applied drops, gels or ointments which may be used to deliver therapeutic material to these regions. An opening in the tymapanic membrane is a very frequent procedure done on a office-visit basis, in cases such as infections of the middle ear (usually in children). The opening closes spontaneously after a few days.

In the presently described use of GDNF protein product of the treatment of inner ear disease or injury it is also advantageous that a topically applied formulation include an agent to promote the penetration or transport of the therapeutic agent into the middle and inner ear. Such agents are known in the art. For example, Ke et al., U.S. Pat. No. 5,1221,696 disclose the use of materials to enhance the penetration of ophthalmic preparations through the cornea.

Inner-ear systems are those systems which are suitable for use in any tissue compartment within, between or around the tissue layers of the inner-ear, such as the cochlea and vestibular organ. These locations include the different structures of the cochlea such as the stria vascularis, Reissner's membrane. organ of Corti, spiral ligament and the cochlear neurons. An invasive procedure might not be required to access those structures since it has been shown that protein do penetrate the membrane of the round window into the perylimph of the inner ear. A particularly suitable vehicle for introducing GDNF into the inner ear by penetration through the round window membrane is artificial perylimph. This solution consists of 10.00 mM D-glucose, 1,5 mM CaCl, 1.5 mM MgCl in a 1.0% solution of Dulbeco's phosphate-buffered saline in deionized water at 280–300 mOsm and pH of 7.2. Yet another preparation may involve the formulation of the GDNF protein product with an agent, such as injectable microspheres or liposomes into the middle ear, that provides for the slow or sustained release of the protein which may then be delivered as a depot injection. Other suitable means for the inner-ear introduction of GDNF protein product includes, implantable drug delivery devices or which contain the GDNF protein product, and a cochlear-implant with a tunnel through, so GDNF can be continuously delivered through it to the inner ear.

The ear-treatment preparations of the present invention, particularly topical preparations, may include other components, for example middle-ear acceptable preservatives, tonicity agents, cosolvents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Sufficient tonicity enhancing agent is advantageously added so that the formulation to be instilled into the ear is compatible with the osmolarity of the endo- and perilymph. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents include, but are not limited to, glycerin, propylene glycol and polyethylene glycol. Suitable complexing agents include caffeine, polyvinylpyrrolidone, beta -cyclodextrin or hydroxypropyl-beta -cyclodextrin. The buffers can be conventional buffers such as borate, citrate, phosphate, bicarbonate, or Tris-HCl.

The formulation components are present in concentration that are acceptable to the middle or inner ear site of administration. For example, buffers are used to maintain the composition at physiological pH or at slightly lower pH, typically within a pH range of from about 5 to about 8.

Additional formulation components may include materials which provide for the prolonged residence of the middle ear administered therapeutic agent so as to maximize the topical contact and promote absorbtion through the round window membrane. Suitable materials include polymers or gel forming materials which provide for increased viscosity of the middle-ear preparation. The suitability of the formulations of the instant invention for controlled release (e.g., sustained and prolonged delivery) of an inner-ear treating agent can be determined by various procedures known in the art. Yet another ear preparation may involve an effective quantity of GDNF protein product in a mixture with non-toxic middle-ear treatment acceptable excipients which are suitable for the manufacture of tablets. By dissolving the tablets in sterile water, or other appropriate vehicle, middle-ear treatment solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia.

Administration/Delivery of GDNF Protein Product

The GDNF protein product may be administered parenterally via a subcutaneous, intramuscular, intravenous, transpulmonary, transdermal, intrathecal or intracerebral route. For the treatment of inner-ear conditions, the GDNF protein product may be administered into the middle-ear (or directly into the inner-ear, especially in cases where invasive procedure is already in place), by topical application, inserts, injection, implants, cell therapy or gene therapy. For example, slow-releasing implants containing the neurotrophic factor embedded in a biodegradable polymer matrix can deliver GDNF protein product. GDNF protein product may be administered extracerebrally in a form that has been modified chemically or packaged so that it passes the blood-brain barrier, or it may be administered in connection with one or more agents capable of promoting penetration of GDNF protein product across the barrier. Similarly, the GDNF protein product may be administered in the middle or inner ear, or it may be administered on top of the tympanic membrane in connection with one or more agents capable of promoting penetration or transport of GDNF protein product across the membranes of the ear. The frequency of dosing will depend on the pharmacokinetic parameters of the GDNF protein product as formulated, and the route of administration.

The specific dose may be calculated according to considerations of body weight, body surface area or organ size. Further refinement of the calculations necessary to determine the appropriate dosage for treatment involving each of the above mentioned formulations is routinely made by those of ordinary skill in the art and is within the ambit of tasks routinely performed, especially in light of the dosage information and assays disclosed herein. Appropriate dosages may be ascertained through use of the established assays for determining dosages utilized in conjunction with appropriate dose-response data. It will be appreciated by those skilled in the art that the dosage used in inner-ear administered formulations will be minuscule as compared to that used in a systemic injection or oral administration.

The final dosage regimen involved in a method for treating the above-described conditions will be determined by the attending physician, considering various factors which modify the action of drugs, e.g., the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of GDNF may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein which have the effect of continuous presence, in predictable amounts, based on a determined dosage regimen. Thus, GDNF protein products include proteins derivatized or otherwise formulated to effectuate such continuous administration.

GDNF protein product cell therapy, e.g., middle- or inner ear implantation of cells producing GDNF protein product, is also contemplated. This embodiment would involve implanting into patients cells capable of synthesizing and secreting a biologically active form of GDNF protein product. Such GDNF protein product-producing cells may be cells that are natural producers of GDNF protein product (analogous to B49 glioblastoma cells) or may be recombinant cells whose ability to produce GDNF protein product has been augmented by transformation with a gene encoding the desired GDNF protein product in a vector suitable for promoting its expression and secretion. In order to minimize a potential immunological reaction in patients being administered GDNF protein product of a foreign species, it is preferred that the natural cells producing GDNF protein product be of human origin and produce human GDNF protein product. Likewise, it is preferred that the recombinant cells producing GDNF protein product be transformed with an expression vector containing a gene encoding a human GDNF protein product. Implanted cells may be encapsulated to avoid infiltration of surrounding tissue. Human or non-human animal cells may be implanted in patients in biocompatible, semipermeable polymeric enclosures or membranes that allow release of GDNF protein product, but that prevent destruction of the cells by the patient's immune system or by other detrimental factors from the surrounding tissue. Such an implant, for example, may be attached to the round-window membrane of the middle-ear to produce and release GDNF protein product directly into the perilymph.

It is also contemplated that the patient's own cells may be transformed ex vivo to produce GDNF protein product and would be directly implanted without encapsulation. For example, organ of Corti supporting cells may be retrieved, the cells cultured and transformed with an appropriate vector and transplanted back into the patient's inner ear where they would produce and release the desired GDNF protein or GDNF protein variant.

GDNF protein product gene therapy in vivo is also envisioned, by introducing the gene coding for GDNF protein product into targeted inner ear cells via local injection of a nucleic acid construct or other appropriate delivery vectors. (Hefti, *J. Neurobiol.*, 25:1418–1435, 1994). For example, a nucleic acid sequence encoding a GDNF protein product may be contained in an adeno-associated virus vector or adenovirus vector for delivery to the inner ear cells. Alternative viral vectors include, but are not limited to, retrovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and 5,106,627, each of which is specifically incorporated herein by reference. A system for encapsulating living cells is described in PCT Application WO 91/10425 of Aebischer et al., specifically incorporated herein by reference. See also, PCP Application WO 91/10470 of Aebischer et al., Winn et al., *Exper. Neurol.*, 113:322–329, 1991, Aebischer et al., *Exper. Neurol.*, 111:269–275, 1991; Tresco et al., *ASAIO*, 38:17–23, 1992, each of which is specifically incorporated herein by reference. Techniques for formulating a variety of other sustained- or controlled-delivery means, such as liposome carriers, bio-erodible particles or beads and depot injections, are also known to those skilled in the art.

It should be noted that the GDNF protein product formulations described herein may be used for veterinary as well as human applications and that the term "patient" should not be construed in a limiting manner. In the case of veterinary applications, the dosage ranges should be the same as specified above.

Other aspects and advantages of the present invention will be understood upon consideration of the following illustrative examples. Example 1 addresses the effects of GDNF protein product administration on hair cells in a Cochlea explant culture system. Example 2 addresses the effects of GDNF protein product administration on spiral ganglion neurons, in a dissociated cell culture generated from cochlea. The results of the organ of Corti explant cultures studies and that of the adult rat spiral ganglion neuronal cultures demonstrated that GDNF protein product has neurotrophic and protective activity for the auditory neurons and the hair cells of the organ of Corti against ototoxins, which were not previously known to be GDNF-responsive.

EXAMPLES

Example 1

GDNF Protein Product Protects Cochlear Hair Cells Against Ototoxicity

MATERIALS

The materials used in the following Example were obtained as follows.

Organ of Corti dissecting solution:

Dulbecco's Phosphate Buffered Saline (PBS; 1x, without calcium chloride, without magnesium chloride. Cat. #14190-136, Gibco BRL), containing 1.5 g/L D-Glucose (Dextrose. Cat. #15023-021, Gibco BRL).

Organ of Corti explant culture Medium

1. High glucose Dulbecco's Modified Eagle Medium (DMEM; 1 X, with L-glutamine, without Sodium Pyruvate. Cat. #11965-084, Gibco BRL)

2. 0.15 g/100 ml of D-Glucose (Dextrose. Cat. #15023-021, Gibco BRL)

3. 1% N-2 Supplement (100 X, Cat. #17502-030, Gibco BRL)

4. 100 Units/ml of Penicillin G, Potassium (Penicillin; Cat. # 21840-020, Gibco BRL)

METHODS

Preparation of Medium

DMEM was supplemented with 1% N-2 supplement, and D-glucose was added to a final concentration of 1.5 g/L. Penicillin was added at 100 Units/ml. After mixing, the medium was filtered and kept at 4° C. The medium was prepared fresh just before use in order to minimize inter-experimental variations. Plastic pipettes and containers were used throughout to minimize protein adsorption.

GDNF Protein Product Solutions

Purified human recombinant GDNF protein products were prepared as 1 mg/ml solutions in D-PBS (phosphate buffered saline prepared with distilled water) containing five percent bovine serum albumin. The solutions were stored at −85° C. in aliquots. Serial dilutions (0.1; 1; 10; 25; 50 ng/ml in normal culture medium) were prepared in 96 microplates. Ten microliters of ten-fold concentrated GDNF protein product solutions were added to Organ of Corti explant cultures medium containing ototoxins or not (control) (90 μl). Control cultures received normal medium (10 μl). The GDNF protein product treatments were initiated on day of plating. On the second day, media were exchanged into media containing the ototoxins alone, together with GDNF or without both (control).

Dissecting tools and culture dishes

1. The 4" and 5" dissecting forceps and 4" dissecting scissors were from Roboz Surgical, Washington, DC.

2. Falcon sterile 96-well microplates (Flat Bottom. Cat. #3072), tissue culture plastic ware and polypropylene centrifuge tubes were from Beckton-Dickinson, Lincoln Park, N.J.

Ototoxins and Related Reagents

1. Neomycin solution (Cat. #N1142, Sigma. St. Louis, Mo.), used at final concentration of 0.6 mM (A fresh solution was made each experiment by adding 90 μl of 1 mg/ml neomycin and to 1410 μl medium).

2. Cisplatin (Platinol-AQ. Cat. #NDC 0015-3220-22, Bristol-Myers Squibb Laboratories, Princeton, N.J.). Used at a final concentration of 35 μg/ml (a fresh solution was prepared each experiment by adding 52.5 μl of 1 mg/ml cisplatin to 1447.5 μl medium)

3. Triton X-100 (t-Octylphenoxypoly-ethoxyethanol. Cat. #X-100, Sigma. St. Louis, Mo.)

4. Phalloidin (FITC Labeled. Cat. #P-5282, Sigma. St. Louis, Mo.)

5. Vectashield (Mounting Medium, Cat. #H-1000, Vector, Burlingame, Calif.)

Preparation of Rat Organ of Corti explant

Organ of Corti explants were obtained from P3-P4 Wistar rats. Rats were decapitated, the lower jaw was cut out and skin removed. The temporal bone was collected in dissection solution, the otic capsule exposed and the bony-cartilaginous cochlear capsule was carefully separated from the temporal bone. Freed cochlea were transferred to another Petri dish with dissection solution for further dissection. Intact organs of Corti were obtained by using a fine forceps to hold central VIII nerve tissue and remove it out, then the stria vascular membrane was carefully stripped off, starting from the apex or base. The organ of Corti then was then transferred to a 35-mm diameter Petri dish containing cold PBS supplemented with glucose and ready to be cultured.

Cochlea explant culture procedure

Cochlea explants were cultured in uncoated 96 microplates. A single organ of Corti was placed in a well and was kept floating in the medium. Explants were kept in normal medium for 24 hours (90 μl/well). GDNF protein solution (10 μl) was added to the 'treated' cultures and 10 μl medium was added to controls. After 24 hours of incubation, the media were changed and the explants were exposed to ototoxin-containing medium (90 μl), with GDNF protein solution (10 μl) or without (control). The cultures were incubated for an additional 3 days. The explants were then fixed with 4% paraformaldehyde in 0.1 M D-PBS for 30 minutes at room temperature and processed for immunostaining.

FITC-phalloidin staining of hair cells

To identify and count hair cells in the organ of Corti, a direct immunostaining method was used to label the actin present naturally in the stereocilia bundles of the hair cells. The explants were washed three times with D-PBS (200 μl per well) and permeabilized with 1% Triton X-100 in D-PBS for 15 minutes at room temperature. After three washes in D-PBS, the explants were incubated with FITC-labeled Phalloidin (1:60 from stock, 50 μl/well) for 45 minutes at room temperature. The plates were covered with aluminum foil as the Phalloidin is light sensitive. After three more washes with D-PBS, the labeled explants were placed in a drop of glycerol on a microscope slide, covered with a glass coverslip and sealed with nail polish. The explants were observed under a Nikon Diaphot-300 inverted fluorescence microscope, using FITC filters and fluorescence optics.

Determination of hair cell number

For each experimental point, 2 to 4 cochlea were used. In each cochlea, the number of hair cells was counted in 2–3 section, 175 μm in length each. Only the sections in the middle turn of the cochlea were analyzed. Each experiment was repeated several times. The numbers of hair cells in control and cisplatin- or neomycin-treated cultures was generated from analyzing 40 cochlea per point.

RESULTS

Hair cells in the floating explant cultures did not die during the experiment period of four days. Thus, the number of phalloidin-stained cells present at the end of the 4 days experiment period, in the absence of ototoxins and treatments, was 105.4±6.9 (n=28). Ototoxins added to the explants on the second day post-plating caused significant loss in hair cell number found after 4 days in vitro. Exposure to 35 μg/ml cisplatin 24 hours after plating caused a loss of about 80 percent of the hair cells: only 21.2%±6.0 (n=40) of the initial number of hair cells survived (Table 2) and after exposure to 0.8 mM neomycin, only 7.4%±4.7 (n=43) of the hair cells survived (Table 2).

TABLE 2

Effect of GDNF on cochlear hair cells exposed to cisplatin

| | Hair Cell Survival (% of untreated) | |
|---|---|---|
| Treatment | GDNF added at time of plating | GDNF added 24 hours after plating |
| Cisplatin alone (35 μg/ml) | 21.3 ± 4.0 (n = 30) | 21.3 ± 4.0 (n = 30) |
| Cisplatin + GDNF, 0.05 ng/ml | 35.2 ± 5.4 (n = 5)* | ND |
| Cisplatin + GDNF, 0.1 ng/ml | 39.6 ± 10.5 (n = 17)* | 37.8 ± 11.8 (n = 5)* |
| Cisplatin + GDNF, 1 ng/ml | 46.7 ± 10.8 (n = 20)* | 51.0 ± 8.0 (n = 4)* |
| Cisplatin + GDNF, 10 ng/ml | 46.7 ± 7.7 (n = 16)* | 49.7 ± 4.6 (n = 5)* |
| Cisplatin + GDNF, 25 ng/ml | ND | 45.0 ± 12.0 (n = 3)* |
| Cisplatin + GDNF, 50 ng/ml | 46.8 ± 10.5 (n = 13)* | ND |

GDNF was introduced to the explant cultures either on the day of plating or 24 hours after plating. Cisplatin (35 μg/ml) was added 24 hours after plating, and the cultures were incubated for an additional 3 days. The hair cells were stained with FITC-phalloidin. The number of hair cells was counted in the middle turn of the cochlea in 2–3 sections of 175 μm each. The results are expressed as the percentage of hair cells present in untreated cultures after 4 days in vitro (105.4 ± 6.9; n = 28). Each number is the mean ± SD of n cochleas.
*Significantly different from cisplatin alone at $p < 0.05$ (t-Test)
ND: not determined There was a marked difference in the morphology of the organs of Corti between this two treatments: while the treatment with neomycin resulted in almost complete loss of hair cells, those that were spared were still organized in the typical four row structure (3 rows of outer hair cells and one row of inner hair cells). Cisplatin treatment, on the other hand, caused a marked disruption of the four-row-structure and the surviving cells were randomly located.

In cultures that received GDNF at the time of plating (pretreatment), a significant number of hair cells survived the 3-day exposure to ototoxins (from day 2 to day 4).In cultures exposed to cisplatin, treatment with GDNF concentrations as low as 0.05 ng/ml caused an increase in surviving hair cells from 21% (untreated cultures) to 35%. Maximal protective activity was reached with 0.1 ng/ml GDNF (41% survival) (Table 3). In cultures exposed to neomycin, GDNF at 0.1 ng/ml increased the number of hair cells from 7% to 22%; maximal GDNF activity (37% survival) was seen with 10 ng/ml GDNF (Table 3). GDNF treatment preserved the four-raw morphology in neomycin-treated cultures, but did not prevent its disruption by cisplatin.

To test further the ability of GDNF to rescue hair cells from ototoxicity, a set of experiments was performed in which GDNF was added 24 hours after plating, at the same time as the cultures were exposed to the toxins (co-treatment). The results indicate that under this experimental paradigm GDNF is capable of rescuing hair cells to the same extent as when given prior to the exposure to the toxins (Tables 2 and 3).

TABLE 3

Effect of GDNF on cochlear hair cells exposed to neomycin

| | Hair Cell Survival (% of untreated) | |
|---|---|---|
| Treatment | GDNF added at time of plating | GDNF added 24 hr after plating |
| Neomycin alone (0.8 mM) | 7.1 ± 4.2 (n = 42) | 7.1 ± 4.2 (n = 42) |
| Neomycin + GDNF, 0.05 ng/ml | 19.5 ± 7.5 (n = 6)* | 23.0 ± 6.2 (n = 3)* |
| Neomycin + GDNF, 0.1 ng/ml | 22.0 ± 4.1 (n = 13)* | 27.0 ± 14.7 (n = 3)* |
| Neomycin + GDNF, 1 ng/ml | 28.2 ± 6.1 (n = 19)* | 26.2 ± 6.4 (n = 4)* |
| Neomycin + GDNF, 10 ng/ml | 37.4 ± 4.8 (n = 11)* | ND |
| Neomycin + GDNF, 50 ng/ml | 34.4 ± 5.3 (n = 7)* | ND |

GDNF was introduced to the explant cultures either on the day of plating (pretreament) or 24 hours after plating (co-treatment). Neomycin (0.8 M) was added 24 hours after plating, and the cultures were incubated for an additional 3 days. The hair cells were stained with FITC-phalloidin. The number of hair cells was counted in the middle turn of the cochlea in 2–3 sections of 175 μm each. The results are expressed as the percentage of hair cells present in untreated cultures after 4 days in vitro (105.4 ± 6.9; n = 28). Each number is the mean ± SD of n cochleas.
*Significantly different from neomycin alone at $p < 0.05$ (t-Test)
ND: not determined Example 2

GDNF Protein Product Promotes Survival of Inner Ear Auditory Neurons (Spiral Ganglion Neurons) and Protects Them Against Ototoxins

MATERIALS

The materials used in the following Example were obtained as follows.

Cell Culture Media

High glucose Dulbecco's Modified Eagle's Medium (DMEM; #11965-092), Ham's F12 medium (F12; #117650-21), B27 medium supplement (#17504-010), penicillin/streptomycin (#15070-014), L-glutamine (#25030-016), Dulbecco's phosphate-buffered saline (D-PBS; #14190-052), mouse laminin (#23017-015), bovine serum albumin and fractionV (#110-18-017) were all from GIBCO/BRL, Grand Island, N.Y. Heat-inactivated horse serum was from HyClone, Logan, Utah. Poly-L-ornithine hydrobromide (P-3655), bovine insulin (I-5500), human transferrin (T-2252), putrescine (P-6024), progesterone (P-6149) and sodium selenite (S-9133) were all from Sigma Chemical Company, Saint-Louis, Mo. Papain, deoxyribonuclease I (DNAase) and ovalbumin (Papain dissociation system) were from Worthington Biochemicals, Freehold, N.J. Falcon sterile 96-well microplates (#3072), tissue culture plastic ware and polypropylene centrifuge tubes were from Beckton-Dickinson, Oxnard, Calif. Nitex 20 μm nylon mesh (#460) was from Tetko, Elmsford, N.Y. The 4" dissecting forceps and 4" dissecting scissors were from Roboz Surgical, Washington, DC.

Antibodies and Related Reagents

Neuronal Specific Enolase (NSE) rabbit polyclonal antibody, was from Chemicon (#AB951), biotinylated goat anti-rabbit IgG (#BA-1000) and peroxidase-conjugated avidin/biotin complex (ABC Elite; kit PK-6100) were from Vector Laboratories, Burlingame, Calif. 3',3'-diaminobenzidine was from Cappel Laboratories, West Chester, Pa. Superblock blocking buffer in PBS (#37515) was from Pierce, Rockford, Ill. Triton X-100 (X100), Nonidet P-40 (N6507) and hydrogen peroxide (30%, v/v; H1009) were from Sigma. All other reagents were obtained from Sigma Chemical Company (Saint-Louis, Mo.), unless otherwise specified.

Ototoxins

Cisplatin (Platinol-AQ, #NDC 0015-3220-22) was from Bristol-Myers-Squibb, Princeton, N.J., sodium salicylate was from J. T. Baker, Phillipsburg, N.J. (#3872-01) and neomycin was from Sigma (#N1142).

METHODS

Preparation of Media

A basal medium was prepared as a 1:1 mixture of DMEM and F12 medium, and was supplemented with B27 medium supplement added as a 50-fold concentrated stock solution. The B27 medium supplement consists of biotin, L-carnitine, corticosterone, ethanolamine, D(+)-galactose, reduced glutathione, linoleic acid, linolenic acid, progesterone, putrescine, retinyl acetate, selenium, T3 (triodo-1-thyronine, DL-alpha-tocopherol; vitamin E), DL-alpha-tocopherol acetate, bovine serum albumin, catalase, insulin, superoxide dismutase and transferrin. L-glutamine was added at a final concentration of about 2 mM, penicillin at about 100 IU/l, and streptomycin at about 100 mg/l. Heat-inactivated horse serum was added to a final concentration of about 2.5 percent, D-glucose was added to a final concentration of about 5 g/l, HEPES buffering agent was added to a final concentration of about 20 mM, bovine insulin was added to a final concentration of about 2.5 mg/ml, and human transferrin was added to a final concentration of about 0.1 mg/ml. After mixing, the pH was adjusted to about 7.3 and the medium was kept at 4° C. The media were prepared fresh just before use in order to minimize inter-experimental variations. Plastic pipettes and containers were used throughout to minimize protein adsorption.

GDNF Protein Product Solutions

Purified human recombinant GDNF protein products were prepared as 1 mg/ml solutions in D-PBS (phosphate—buffered saline prepared with distilled water) containing five percent bovine serum albumin. The solutions were stored at −85° C. in aliquots. Serial dilutions were prepared in 96-well microplates. Ten microliters of ten-fold concentrated GDNF protein product solutions were added to cell cultures containing culture medium (90 µl). Control cultures received D-PBS with 5 percent albumin (10 µl). The GDNF protein product treatments were added to the cultures one hour after cells were seeded or 24 hours later, alone or together with the ototoxins.

Ototoxins preparations

Neomycin was added straight from the stock solution (about $10^{-3}$ M) at 10 µl per well to result in a final concentration of about $10^{-4}$ M. Cisplatin was diluted with culture medium from the stock solution (1 mg/ml) to a solution of 20 µg/ml and added at 10 µl per well, to result in a final concentration of 2 µg/ml. Sodium salicylate was prepared from powder to a stock solution of 1M in PBS and further diluted in the culture medium to 100 mM, which resulted in a 10 mM final concentration when added at 10 µl/well to the culture.

Culture Substratum

To encourage optimal attachment of spiral ganglion cells on substratum and neurite outgrowth, the microtiter plate surfaces (the culture substratum) were modified by sequential coating with poly-L-ornithine followed by laminin in accordance with the following procedure. The plate surfaces were completely covered with a 0.1 mg/ml sterile solution of polyornithine in 0.1 M boric acid (pH 8.4) for at least one hour at room temperature, followed by a sterile wash with Super-Q water. The water wash was then aspirated and a 10 µg/ml solution of mouse laminin in PBS was added and incubated at 37° C. for two hours. These procedures were conducted just before using the plates in order to ensure reproducibility of the results.

Preparation of Rat Spiral Ganalion Cell Cultures

Three- to four-week-old Wistar rats (obtained from Jackson Laboratories, Bar Harbor, Me.) were injected with overdose of the following solution (ketamine (100 mg/ml); Xylazine (20 mg/ml) and Acopromazine Maleate 910 mg/ml) at 3:3:1 proportions), killed by decapitation and the temporal bone with the cochlea were dissected out and transferred sterilely into PBS with 1.5 g/L glucose on ice. A maximum of 30 cochlea were processed per experiment. The cochlea were opened and the organ of Corti with the bony modiolus was collected into 50 ml sterile tube containing 5 ml dissociation medium (120 units papain and 2000 units DNAase in HBSS). The tissue was incubated for 30 minutes at about 37° C. on a rotary platform shaker at about 200 rpm and then the dissociation solution was replaced with a fresh one and the incubation resumed for another 30 min. The cells were then dispersed by trituration through fire-polished Pasteur pipettes, sieved through a 40 µm Nitex nylon mesh to discard undissociated tissue, and centrifuged for five minutes at 200×g using an IEC clinical centrifuge. The resulting cell pellet was resuspended into HBSS containing ovalbumin and about 500 units DNAase, layered on top of a four percent ovalbumin solution (in HBSS) and centrifuged for about 6 minutes at 500×g. The final pellet was resuspended into about 6 ml of the culturing medium and seeded at 90 µl/well in the precoated plates.

Immunohistochemistry of spiral ganglion cells

Spiral ganglion neurons were identified by immunohistochemical staining for neuronal specific enolase (NSE). Cultures of spiral ganglion cells were fixed for about 10 minutes at room temperature with eight percent paraformaldehyde in D-PBS, pH 7.4, added at 100 µl/well to the culture medium and then replaced by 100 µl of four percent paraformaldehyde for additional 10 minutes, followed by three washes in D-PBS (200 µl per 6-mm well). The fixed cultures were then incubated in Superblock blocking buffer in PBS, containing one percent Nonidet P-40 to increase the penetration of the antibody. The rabbit polyclonal anti-NSE antibodies (Chemicon) were then applied at a dilution of 1:6000 in the same buffer, and the cultures were incubated for two hours at 37° C. on a rotary shaker. After three washes with D-PBS, the spiral ganglion cell-bound antibodies were detected using goat-anti-rabbit biotinylated IgG (Vectastain kit from Vector Laboratories, Burlingame, Calif.) at about a 1:300 dilution. The secondary antibody was incubated with the cells for about one hour at 37° C., and the cells were then washed three times with D-PBS. The secondary antibody was then labeled with an avidin-biotin-peroxidase complex diluted at 1:300, and the cells were incubated for about 60 minutes at 37° C. After three more washes with D-PBS, the labeled cell cultures were reacted for 5 minutes in a solution of 0.1 M Tris-HCl, pH 7.4, containing 0.04% 3',3'-diaminobenzidine-(HCl)4, 0.06 percent NiCl2 and 0.02 percent hydrogen peroxide.

Determining spiral Ganglion Cell Survival

After various times in culture (24 hours, 3 days and 4 days), rat spiral ganglion cell cultures were fixed, processed and immunostained for NSE as described above, and the cultures were then examined with bright-light optics at 200× magnification. All the NSE-positive neurons present in a 6-mm well were counted. Viable spiral ganglion cells were characterized as having a round body of size ranging from 15–40 μm and bearing neuritic processes. Spiral ganglion cells showing signs of degeneration, such as having irregular, vacuolated perikarya or fragmented neurites, were excluded from the counts (most of the degenerating spiral ganglion cells, however, detached from the culture substratum). Cell numbers were expressed either as cells/6-mm well or as the fold-change relative to control cell density.

RESULTS

Cultures of rat spiral ganglion neurons were used to demonstrate the effect of GDNF protein product on survival and protection against ototoxins. The spiral ganglion cells were obtained from three to four-week old rat cochlea. The dissociated cells were then seeded into polyornithine-laminin-coated microplates at a density of about 1 cochlea per 2 wells in DMEM/F12 supplemented with B27 medium supplement, 2.5 percent heat-inactivated horse serum, D-glucose, HEPES, insulin and transferrin. The cultures consisted of a mixture of neurons and non-neuronal cells. However, the only neurons present were spiral ganglion neurons and were identified by the presence of NSE immunoreactivity. At the concentration seeded(1 dissociated organ of Corti into 2 wells), the number of NSE-positive cells per well 24 hours after seeding was 127±17 (n=7) under control conditions (no added treatments). At the end of the experiment, 4 days after seeding, the number of the neurons per well was reduced to 64±4.7, which represents 50.5%±3.7 of the number present after 24 hours in vitro, under control conditions.

The effect of GDNF protein product administration was assessed on the survival and morphological maturation of cultured rat spiral ganglion neurons, as well as on their ability to resist the toxic effect of a known ototoxin such as cisplatin. Cultures of spiral ganglion cells were treated 24 hours after seeding with human recombinant GDNF protein product (ranging from 50 ng/ml to 0.1 ng/ml) alone, or in combination with cisplatin (35 μg/ml). Twenty four hours after seeding, there was no difference in the number of auditory neurons between control cultures and those treated with GDNF at 1 ng/ml and 10 ng/ml (127±17; 126±24 and 125±19 neurons/well respectively). After an additional period of 3 days, treatment with GDNF at a concentration of 1 ng/ml did not result in a significant increase in neuronal cell number. There was however, a marked trophic effect: the neuronal soma were larger and fibers longer and more elaborate than in control cultures. In cultures treated with 10 ng/ml GDNF, about 72% of the neurons present after 24 hours survived, representing a 44% increase over control cultures (Table 4). The trophic effect was even stronger than in cultures treated with 1 ng/ml GDNF.

GDNF also protected spiral ganglion neurons from cisplatin toxicity (Table 4). Exposure of cultures to 5 82 g/ml cisplatin 24 hours after seeding resulted in the loss of about 94% of the initial number (at 24 hours) of the neurons after 4 days in culture. When GDNF was added together with the cisplatin, the number of neurons found after 4 days was significantly higher. This protective effect of GDNF was dose-dependent: 20.1±5.1; 27.5±3.2 and 32.8±1.0 of the neurons present at the beginning of the toxic treatment were found with GDNF concentrations of 1 ng/ml, 10 ng/ml and 25 ng/ml respectively (data not shown). These results indicate that about 63 percent of the neurons that respond to GDNF (about 44% of the spiral ganglion neuron population) can also be protected against cisplatin toxicity.

TABLE 4

Effect of GDNF on spiral ganglion neuron survival

| | Spiral Ganglion Neuron Survival (% of initial number after 24 hours) | |
| --- | --- | --- |
| Treatments | None | Cisplatin (5 μg/ml) |
| None | 48.5 ± 4.5 (n = 9) | 6.1 ± 1.2 (n = 3) |
| GDNF, 10 ng/ml | 71.6 ± 7.4** (n = 5) | 32.8 ± 1.0* (n = 3) |

GDNF and cisplatin were added to dissociated spiral ganglion neuron cultures 24 hours after plating. The cultures were incubated for an additional 3 days and the number of neurons was determined by counting NSE-immunoreactive cells. Neuronal cell numbers are expressed as the percentage of neurons present after 24 hours in vitro. Each result is the mean ± SD of n cultures.
*Significantly different from cisplatin alone at $p < 0.05$ (t-Test)
**Significantly different from untreated control at $p < 0.05$ (t-Test)

Example 3

GDNF Protein Product Promotes In Vivo Survival of Cochlear Hair Cells

The following example demonstrates that the inner ear administration of GDNF protein product protects cochlear hair cells against ototoxicity in an animal model. GDNF was introduced into the inner ear via a cannula pushed into the scala tymapni through a hole drilled in the basal turn of the cochlea. The cannula was connected to an Alzet mini-pump loaded with GDNF (50 ng/ml) at a releasing rate of 0.5 μl/hour for 14 days. Cisplatin i.m. injections were started two days after the cannulation, at either 1 mg/ml daily for 15 days or at 7.5 mg/kg twice, at a 5 days interval (inset of FIG. 2). The experiment was terminated after 27 days. The hair cells were stained with FITC-phalloidin, and their number was determined in the middle turn of the cochlea (in at least 20% of the middle turn part). The results are expressed as the percent of hair cells lost for each individual guinea pig for the GDNF treated ear (right ear) and the untreated ear (left ear).

MATERIALS

The materials used in the following Example were obtained as follows

Mini-pump Preparation Materials:

Medical vinyl tubing size V/4, catalog No BB317-85, was from Bolab Products [(800) 331-7724]. Fisher brand 5 ml plastic pipettes were used. Microlumen Polyimide tubing, catalog #8004853 OG (Tampa Fla.) was used. Silicone Medical Product MDX 4-4210, was from Dow Corning Corporation, Midland, Mich. Alzet osmotic mini-pump flow moderator and Alzet osmotic mini-pump, Catalog No 2002, were from Alza Corp., Palo Alto, Calif. Tape (TimeMed tape). Prosil-28, Product No 11975-0, was from PCR Incorporated, Gainesville Fla. Purified human recombinant GDNF protein products were prepared as a 50 ng/ml solution in D-PBS and 0.1% BSA. Sterile 0.1% methylene blue (catalog # M-9140) dissolved in PBS, and mineral oil (catalog # 400-5), were from Sigma.

Mini-pump preparation Procedure:

Vinyl tubing was cut into an approximately four inch section and placed through a miniature vise. A piece of the Microlumen Polyimide tube (7 mm) was placed into the end of the vinyl tube. Silicone was mixed by adding approximately 10 parts of base and one part of curing agent. A droplet was placed at the opening of the vinyl tube using a fine probe, and the Microlumen tube was pushed into the vinyl, leaving 3.75 mm length extending from the vinyl tube. Using a drop of Silicone on the probe, a small ball was created around the Microlumen tube, 0.5 mm from the tip, and allowed to dry over night.

The diameter of a 5 ml pipette was increased by applying three concentric layers of tape down the length of the pipette. A constant gap was left where the pipette remains uncovered. V/4 tubing was wrapped around the pipette, and the coils were adjusted so that there were two loose ends of tubing and there was a continuous contact between all coils. Two thin strips of tape were aligned with the edges of the tape on the pipette, to secure the coil in place. Two thin lines of super glue were applied evenly on the coils. After drying for a minimum of one hour, the loose ends were aligned approximately parallel to the pipette and secured in place with one strip of tape. A drop of super glue was applied to secure the tubing to the coils. Following overnight drying, the tape was removed and the coils were slid off the pipette. A flow moderator was inserted into one of the loose ends and secured with one drop of super glue.

The coils were flushed with 1% Prosil-28 in water, rinsed thoroughly with water and then flushed with 70% ethanol. The ethanol was removed by means of a syringe or air vacuum. Coils were left in the desiccator with air vacuum on for at least 30 minutes and were kept overnight in the closed and tight desiccator followed by gas sterilization. During the loading procedure, the coil device was kept horizontal as much as possible to prevent gravity driven movement of the liquids of GDNF, oil, and dye. The formation of air bubbles in the pump or coils was avoided. The pump was submerged in sterile PBS and incubated overnight at 37° C.

The loading of a pump with methylene dye was done by holding the pump in a vertical position. A dye-loaded syringe was inserted completely into the pump, and the dye was injected until the pump overflowed. Injection of any air bubbles into the pump was avoided. A short piece of sterile V/4 tubing was placed onto the Flow Moderator. GDNF was loaded at a concentration of 50 ng/ml in PBS+0.1% BSA, in a total volume of 230 $\mu$l, to within about 10 mm of the cannula tip, using a syringe connected with V/4 tubing. For vehicle control experiments, the same volume of PBS+0.1% BSA was loaded into the pumps. The short piece of V/4 tubing was removed. Mineral oil was then loaded into the coil device with a syringe in such a way that a 2 mm air space and 7 mm of mineral oil were interposed between the pump fluid and the line fluid (infusion fluid). A Flow moderator was inserted completely into the pump.

PUMP INSERTION IN INNER EAR
Materials:
Tissue adhesive glue—Cyanoacrylate, was from Vetbond Tissue Adhesive, 3M Animal Care Products, St. Paul, Minn. Carboxylate cement ESPE Durelon, catalog #03828, was from ESPE-Premier Sales Corp., Norristown Pa. Methyl methacrylate was from Lang Jet Acrylic, Lang Dental MFG, Co., Wheeling, Ill. Dissecting tools were from Roboz Surgical. Xylazine, ketamine and buprenorphine were used. Lubricant Ophthalmic Ointment (AKWA Tears) was from Akorn Inc., Abita Springs La. Xylocaine 2%, catalog No NDC 0186-0160-01, was from ASTRA. Medical Grade Silicone Grease, Art. No. 51.300, was from Unimed. Durelon Pulver powder carboxylate-cement, catalog No. D-82229, was from ESPE, Seefeld. Sulfate ointment (Bacitracin Zinc-neomycin, catalog No. 0168-0012-31) was from Fougera.

Procedure:
Albino guinea pigs (250–350 g) were anesthetized with a mixture of xylazine 10 mg/kg, ketamine 40 mg/kg and buprenorphine 0.05 mg/kg. The right ear area was shaved caudally, starting about 2 cm anterior to vertex, 4–5 cm posterior to scapulae and postauricularly. The shaved area was washed with Betadine. Lubricant ophthalmic ointment was applied to both eyes. Xylocaine was injected subcutaneously into the tissue to be incised. Using aseptic technique, a post-auricular incision was made. Using a fine needle, a hole was drilled into the bulla to expose the middle ear cavity and visualize the cochlea. A small hole was drilled manually into the bone wall of the basal turn, below the round window using a fine needle. The tip of the cannula was inserted into the hole until the silicone drop was seated against the bone, which placed the cannula tip about midway into the scala tympani canal. A drop of cyanoacrylate was placed at the bulla hole. Carboxylate cement was placed around the cannula over the cyanoacrylate. Once the cement was hardened, the placement was confirmed, and the rest of the hole was covered with carboxylate cement on top of a layer of silicone grease. A subcutaneous pocket was made between the scapulae to accommodate the pump which was then inserted. The subcutaneous pocket was rinsed once with 3 ml of a solution of nitrofurazone dissolved in sterile PBS and was then filed with 3 ml of sterile PBS plus 1% Gentamycin to discourage infection. The incision was closed with wound clips after nitrofurazone powder was applied around the wound.

DEAFENING:
Materials:
Cisplatin (Platinol-AQ), catalog No NDC 0015-3220-22, was from Bristol-Myers Squibb Laboratories, Princeton. N.J.

Procedure:
Injections of cisplatin (i.p.) were started two days after mini-pump implantation. Two paradigms of application were used: either two 7.5 mg/kg injections made at a 5 days interval, or 1 mg/kg daily, for 15 days.

PERFUSION:
After four weeks, the guinea pigs were deeply anesthetized with a mixture of xylazine and ketamine, and were perfused transcardially with ice-cold PBS followed by ice-cold 4% paraformaldehyde in PBS. Temporal bones were removed, and the bony cochlea was placed in 4% paraformaldehyde for postfixation overnight at 4° C.

STAINING
Surface preparation and Phalloidin staining methods were used to stain hair cells. The bony cochlea was opened by a fine needle or #11 blade. Stria vascularis was removed using a fine forceps. In a petri dish filled with PBS, the basal membrane was carefully dissected out from the boney modiolus, using fine needles. Care was taken to remove it intact. The procedure for Phalloidin staining was similar to that performed for the in vitro explants, with the following changes: permeabilization was done for 20–30 minutes, and Phalloidin was added for 90 minutes. Apex, middle turn and basal turn pieces were mounted on a 60×22 glass coverslip. A drop of VECTASHIELD mounting medium was added, and the samples were covered with a 22×22 mm coverslip and sealed with nail polish to prevent evaporation.

DATA ANALYSIS
Each cochlea was examined under microscope with a FITC filter set. Eight segments with the greatest hair cell loss from midturn of basal membrane were selected and photographed using an attached computer printer. Hair cell counts were performed manually, using the photographs. In each animal, hair cell loss in the left ear (as a control, i.e., without GDNF infusion) was compared to hair cell loss in the right ear (GDNF infused).

RESULTS

The cisplatin injections resulted in a significant loss of hair cells in the cochlea. This loss, in the middle turn sections analyzed in the left ears of three guinea pigs injected with cisplatin at 1 mg/kg daily for 15 days, was 49.2%; 21.2% and 46.9%. Also in the guinea pig injected with cisplatin at a 7.5 mg/kg twice, instead of the 1 mg/kg daily, there was a loss of 42% of hair cells in the left ear. The introduction of GDNF into the right inner ear of each of the guinea pigs, resulted in a significant reduction in the loss of hair cells. The ratio between the number of missing hair cells to total hair cell number counted in the cochlea were as follows: 241/486; 113/530 and 244/513, in the left ear (control), while their counterparts, in the right ear (GDNF treated) were 83/492; 28/498 and 126/512, respectively. These ratios represent an increase in hair cell lose between left and right ear for each animal in the order of x3; x4.2 and x1.9 for the three animals. In the guinea pig injected with 7.5 mg/kg cisplatin, there was also a 2-fold increase in hair cell loss in the untreated ear (left) compared to the treated ear. (See FIG. 2). In animals implanted with a mini-pump filed with vehicle instead of GDNF, there was no difference in the number of hair cells found in the left ear (untreated ear) and the right ear (implanted) ear.

Example 4

GDNF Protein Product Injections into the Middle Ear Promote In Vivo Survival of Cochlear Hair Cells The following example demonstrates that GDNF protein products protect cochlear hair cells against ototoxicity in an animal model when applied into the middle ear. GDNF was introduced into the right middle ear by a single injection through the tympanic membrane at a concentration of 1 mg/ml in PBS+1% BSA in a volume of 125–135 ul. Cisplatin i.m. injections were started a day after the GDNF injection at 7.5 mg/kg, twice, at a 5 days interval. The experiment was terminated three days after the second cisplatin injection. The hair cells were stained with FITC-phalloidin, and their number determined in the middle turn of the cochlea (in at least 20% of the middle turn part). The results (FIG. 3) are expressed as the percent of hair cells lost for each individual guinea pig for the GDNF treated ear (right ear) and the untreated (left ear).

MATERIALS

The materials used in this experiment were the same as those used in Example 3.

Procedure:

Albino guinea pigs (weighing 600–700 g) were anesthetized with a mixture of xylazine 10 mg/kg, ketamine 40 mg/kg and buprenorphine 0.05 mg/kg. Under a surgical microscope, a hole was made in the tympanic membrane of the right ear by inserting a 27 gauge needle into the membrane. In another location of the tympanic membrane, human protein GDNF (at a concentration of 1 mg/ml in PBS+1% BSA) was injected into the middle ear cavity so that the whole cavity was full (125–135 $\mu$l). A few animals were injected with vehicle only (PBS+0.1% BSA) instead of GDNF. The next day, an i.m. injection of cisplatin (7.5 mg/kg) was made. Five days later, a second injection at the same concentration was made. Three days later (8 days of total experiment period), the animals were sacrificed, tissues were fixed and cochlea were analyzed as described in Example 3.

RESULTS

Figure 3:
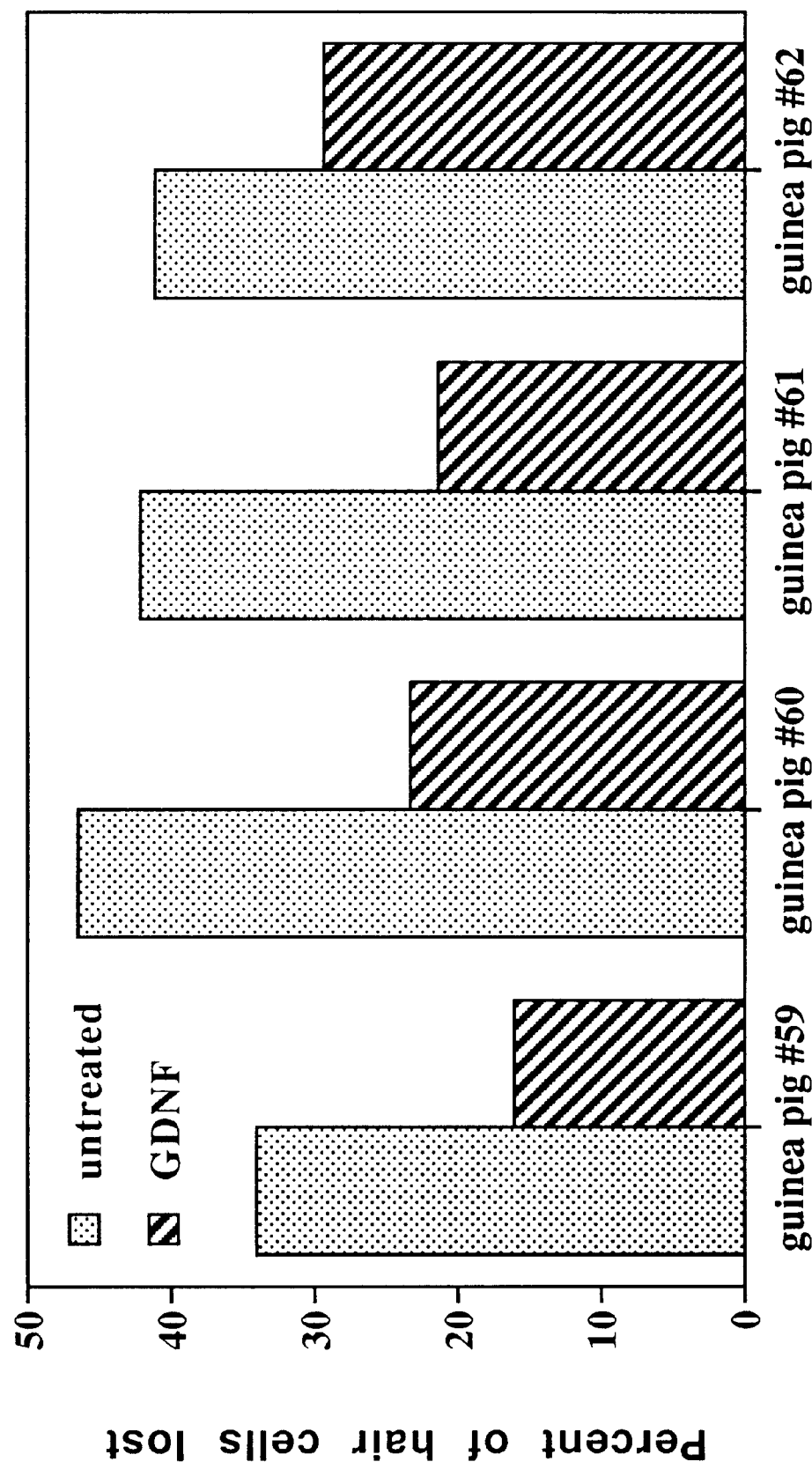
FIG. 3 depicts the results of the study described in Example 4 wherein GDNF protein product injections promote in vivo survival of cochlear hair cells.

At eight days, the four guinea pigs injected with cisplatin displayed a significant loss of hair cells in the cochlea. In the left ears, the ears that did not receive GDNF, the loss of hair cells in the middle turn of the cochlea was: 34%; 47%; 42% and 41%. Injection of GDNF into the cavity of the right middle ear, at 1 mg/ml, reduced this loss significantly: 16%; 23%; 21% and 29%, respectively. (FIG. 3). Guinea pigs that received vehicle injections into the right ear instead of GDNF, did not demonstrate a difference in hair cell number between the right (treated) and left (untreated) ear.

Numerous modifications and variations in the practice of the invention are expected to occur to those skilled in the art upon consideration of the foregoing description of the presently preferred embodiments thereof.

What is claimed is:

1. A method for treating injury or degeneration of cells of the inner ear which may cause hearing loss and/or vestibular symptoms, said method comprising administering a glial cell line-derived neurotrophic factor (GDNF) protein product comprising an amino acid sequence set forth in SEQ ID NO: 1 or an amino acid sequence which is in excess of 70% identical to an amino acid sequence set forth in SEQ ID NO: 1 when up to four gaps in a length of 100 amino acids may be introduced to assist in that alignment, wherein said GDNF protein product promotes the survival or function of cells of the inner ear selected from the group consisting of hair cells of the vestibular apparatus, cochlear hair cells and auditory neurons and wherein the GDNF protein product is administered by cell therapy or gene therapy means wherein cells have been modified to produce and secrete the GDNF protein product.

2. The method of claim 1, wherein said cells are cochlear hair cells.

3. The method of claim 1, wherein said auditory neurons are spiral ganglion neurons.

4. The method of claim 1, wherein the GDNF protein product is in excess of 70% identical to the amino acid sequence set forth in SEQ ID NO: 1.

5. The method of claim 1, wherein the GDNF protein product comprises the amino acid sequence set forth in SEQ ID NO: 1.

6. The method of claim 1, wherein the GDNF protein product further comprises an amino terminal methionine.

7. The method of claim 1, wherein the GDNF protein product is administered at a dose of about 1 µg/kg/day to about 100 mg/kg/day.

8. The method of claim 1, wherein the cells have been modified ex vivo.

9. The method of claim 1, wherein the cells have been modified in vivo.

10. A method for treating cells of the vestibular apparatus, comprising administering a glial cell line-derived neurotrophic factor (GDNF) protein product comprising an amino acid sequence set forth in SEQ ID NO: 1 or an amino acid sequence which is in excess of 70% identical to an amino acid sequence set forth in SEQ ID NO: 1 when up to four gaps in a length of 100 amino acids may be introduced to assist in that alignment, wherein said GDNF protein product promotes the survival or function of hair cells of the vestibular apparatus.

11. The method of claim 10, wherein the disturbance results in dizziness, vertigo or loss of balance.

12. The method of claim 10, wherein the GDNF protein product is in excess of 70% identical to the amino acid sequence set forth in SEQ ID NO: 1.

13. The method of claim 10, wherein the GDNF protein product comprises the amino acid sequence set forth in SEQ ID NO: 1.

14. The method of claim 10, wherein the GDNF protein product further comprises an amino terminal methionine.

15. The method of claim 10, wherein the GDNF protein product is administered at a dose of about 1 µg/kg/day to about 100 mg/kg/day.

16. The method of claim 10, wherein the GDNF protein product is administered by cell therapy or gene therapy means wherein cells have been modified to produce and secrete the GDNF protein product.

17. The method of claim 16, wherein the cells have been modified ex vivo.

18. The method of claim 16, wherein the cells have been modified in vivo.

19. The method of claim 1, wherein said cells are hair cells of the vestibular apparatus.

20. A method for treating injury or degeneration of inner ear cells associated with vestibular symptoms, comprising administering a glial cell line-derived neurotrophic factor (GDNF) protein product comprising an amino acid sequence of SEQ ID NO: 1, wherein said GDNF protein product promotes the survival or function of hair cells of the vestibular apparatus.

* * * * *

UNITED STATES PATENT AND TRADEMARK OFFICE
CERTIFICATE OF CORRECTION

PATENT NO. : 5,929,041
DATED : July 27, 1999
INVENTOR : Ella Magal

It is certified that error appears in the above-identified patent and that said Letters Patent is hereby corrected as shown below:

Cover Page [56], Foreign Patent Documents, add --WO 93/06116 4/1993 WIPO--.

Column 9, Line 52, change "PCT/US92/07488" to --PCT/US92/07888--.

Column 29, Line 60, change "5 82 g/ml" to 5 µg/ml.

Column 35, Lines 43-44, delete "of the inner ear".

Column 35, Lines 53, delete "of the inner ear".

Signed and Sealed this

Eighth Day of February, 2000

Attest:

Q. TODD DICKINSON

Attesting Officer       Commissioner of Patents and Trademarks

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 134 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Ser Pro Asp Lys Gln Met Ala Val Leu Pro Arg Arg Glu Arg Asn Arg
1               5                   10                  15

Gln Ala Ala Ala Ala Asn Pro Glu Asn Ser Arg Gly Lys Gly Arg Arg
            20                  25                  30
```

```
        Gly Gln Arg Gly Lys Asn Arg Gly Cys Val Leu Thr Ala Ile His Leu
            35                  40                  45

Asn Val Thr Asp Leu Gly Leu Gly Tyr Glu Thr Lys Glu Glu Leu Ile
            50                  55                  60

Phe Arg Tyr Cys Ser Gly Ser Cys Asp Ala Ala Glu Thr Thr Tyr Asp
        65                  70                  75                  80

Lys Ile Leu Lys Asn Leu Ser Arg Asn Arg Arg Leu Val Ser Asp Lys
                        85                  90                  95

Val Gly Gln Ala Cys Cys Arg Pro Ile Ala Phe Asp Asp Asp Leu Ser
                    100                 105                 110

Phe Leu Asp Asp Asn Leu Val Tyr His Ile Leu Arg Lys His Ser Ala
                    115                 120                 125

Lys Arg Cys Gly Cys Ile
            130

(2) INFORMATION FOR SEQ ID NO:2:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

TCACCAGATA AACAAATGGC AGTGCTTCCT AGAAGAGAGC GGAATCGGCA GGCTGCAGCT         60

GCCAACCCAG AGAATTCCAG AGGAAAAGGT CGGAGAGGCC AGAGGGGCAA AAACCGGGGT        120

TGTGTCTTAA CTGCAATACA TTTAAATGTC ACTGACTTGG GTCTGGGCTA TGAAACCAAG        180

GAGGAACTGA TTTTTAGGTA CTGCAGCGGC TCTTGCGATG CAGCTGAGAC AACGTACGAC        240

AAAATATTGA AAAACTTATC CAGAAATAGA AGGCTGGTGA GTGACAAAGT AGGGCAGGCA        300

TGTTGCAGAC CCATCGCCTT TGATGATGAC CTGTCGTTTT TAGATGATAA CCTGGTTTAC        360

CATATTCTAA GAAAGCATTC CGCTAAAAGG TGTGGATGTA TC                          402
```